(12) United States Patent
Schirmer et al.

(10) Patent No.: US 7,618,957 B2
(45) Date of Patent: Nov. 17, 2009

(54) PERFLUOROALKYL-CONTAINING COMPLEXES, PROCESS FOR THEIR PRODUCTION AS WELL AS THEIR USE

(75) Inventors: Heiko Schirmer, Berlin (DE); Hanns-Joachim Weinmann, Berlin (DE); Johannes Platzek, Berlin (DE); Ludwig Zorn, Berlin (DE); Bernd Misselwitz, Glienicke (DE); Joerg Meding, Berlin (DE); Heribert Schmitt-Willich, Berlin (DE); Thomas Brumby, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 192 days.

(21) Appl. No.: 11/487,604

(22) Filed: Jul. 17, 2006

(65) Prior Publication Data

US 2007/0189969 A1 Aug. 16, 2007

Related U.S. Application Data

(60) Provisional application No. 60/701,032, filed on Jul. 21, 2005.

(30) Foreign Application Priority Data

Jul. 15, 2005 (DE) .................. 10 2005 033 902

(51) Int. Cl.
*A01N 43/00* (2006.01)
*A61K 31/33* (2006.01)
*C07D 245/00* (2006.01)

(52) U.S. Cl. ...................... 514/183; 540/470
(58) Field of Classification Search ................ None
See application file for complete search history.

(56) References Cited

U.S. PATENT DOCUMENTS

| 6,461,587 B1 | 10/2002 | Platzek et al. |
| 2002/0076380 A1 | 6/2002 | Platzek et al. |
| 2007/0020183 A1* | 1/2007 | Schirmer et al. ......... 424/9.363 |

OTHER PUBLICATIONS

"Sc Isotopes", http://ie.lbl.gov/education/parent/Sc_iso.htm, accessed Jun. 23, 2008.*
"Cr Isotopes", http://ie.lbl.gov/education/parent/Cr_iso.htm, accessed Jun. 23, 2008.*
Greene et al. Protective Groups in Organic Synthesis, 1999, pp. 369-373.*

* cited by examiner

*Primary Examiner*—James O Wilson
*Assistant Examiner*—Noble Jarrell
(74) *Attorney, Agent, or Firm*—Millen, White, Zelano & Branigan, P.C.

(57) ABSTRACT

The invention relates to the subjects that are characterized in the claims, namely perfluoroalkyl-containing metal complexes with nitrogen-containing radicals of general formula I, process for their production and their use in NMR and x-ray diagnosis, radiodiagnosis, and radiotherapy, as well as in MRT lymphography and in blood-pool imaging.

6 Claims, 5 Drawing Sheets

Title Substance from Example 1d; 50 μmol/kg i.v.; T1-TSE (Arrows: Iliac Lymph Nodes with Metastases)

Title Substance from Example 1d; 50 μmol/kg i.v.; T1-TSE; Primary Tumor

Title Substance from Example 1; WHHL Rabbits, 50 µmol/kg i.v.; IR-TFL,

TR/TE/TI = 300/4.0/120 ms, α 20°

Title Substance from Example 14; WHHL Rabbits, 50 µmol/kg i.v.; IR-TFL

TR/TE/TI = 300/4.0/120 ms, α 20°

Title Substance from Example 14; 50 μmol/kg i.v.; T1-TSE, TR-TE 451/8.7 ms, TA 4:48; 24 Hours After Induction of Inflammation; Open Arrows: Inflammation; Closed Arrow: Necrosis

Figure 5

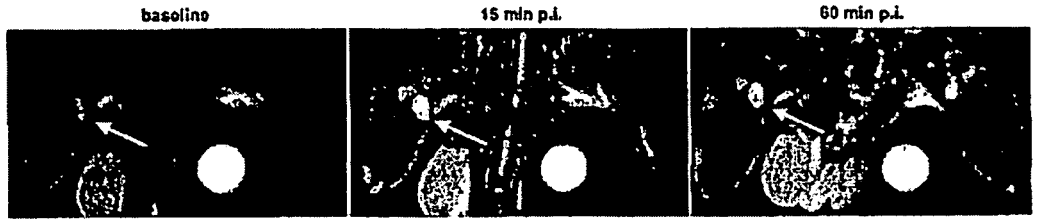

Title Substance from Example 5: 5 μmol/kg i.v.; T1-TSE, TR/TE 451/8.7 ms, TA 3:49; Rats with Stimulated Lymph Nodes; Arrows: Popliteal Lymph Nodes

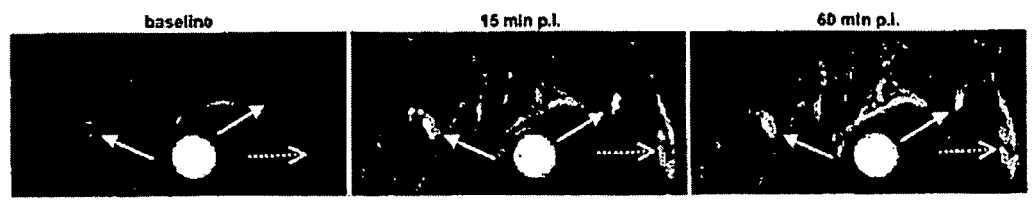

Title Substance from Example 14: 50 μmol/kg i.v.; T1-TSE, TR/TE 451/8.7 ms, TA 4:48; Rats with Stimulated Lymph Nodes; Closed Arrows: Popliteal Lymph Nodes; Open Arrows: Inflammation

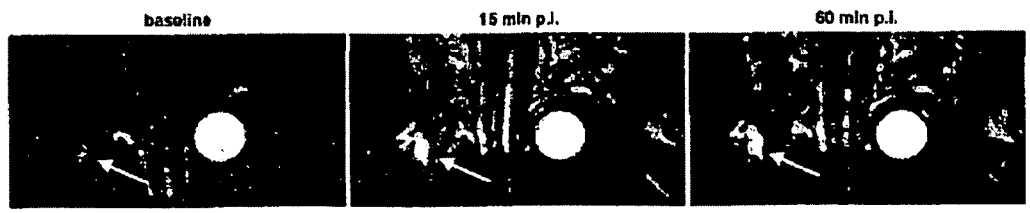

Title Substance from Example 15: 50 μmol/kg i.v.; T1-TSE, TR/TE 451/8.7 ms, TA 4:48; Rats with Stimulated Lymph Nodes; Arrows: Popliteal Lymph Nodes

PERFLUOROALKYL-CONTAINING COMPLEXES, PROCESS FOR THEIR PRODUCTION AS WELL AS THEIR USE

This application claims the benefit of the filing date of U.S. Provisional Application Ser. No. 60/701,032 filed Jul. 21, 2005.

The invention relates to the subjects that are characterized in the claims, namely perfluoroalkyl-containing metal complexes with nitrogen-containing radicals of general formula I, process for their production and their use in NMR and x-ray diagnosis, radiodiagnosis and radiotherapy, as well as in MRT lymphography and in blood-pool imaging. The perfluoroalkyl-containing metal complexes are used in nuclear spin resonance tomography (MRT) for visualizing different physiological and pathophysiological structures and thus for improving diagnostic information, namely the location and the degree of the disease, selection and monitoring of the success of a targeted therapy and for prophylaxis.

The compounds according to the invention are suitable in a quite special way for lymphography, for tumor diagnosis and for infarction and necrosis imaging.

In the field of nuclear magnetic resonance, some fluorine-containing compounds are known that can be used in the area of imaging. In most cases, however, such compounds are proposed only for use in fluorine-19 imaging and are suitable only for this application. Such compounds are disclosed in, for example, U.S. Pat. No. 4,639,364 (Mallinckrodt), DE 4203254 (Max-Planck-Gesellschaft), WO 93/07907 (Mallinckrodt), U.S. Pat. No. 4,586,511 (Children's Hospital Medical Center), EP 307863 (Air Products), U.S. Pat. No. 4,588,279 (University of Cincinnati, Children's Hospital Research Foundation) and WO 94/22368 (Molecular Biosystems).

Additional fluorine-containing compounds that can be used for imaging are disclosed in U.S. Pat. No. 5,362,478 (VIVORX), U.S. Pat. No. 4,586,511, DE 4008179 (Schering), WO 94/05335 and WO 94/22368 (both molecular biosystems), EP 292 306 (TERUMO Kabushiki Kaisha), EP 628 316 (TERUMO Kabushiki Kaisha) and DE 4317588 (Schering).

While no interactions between the two nuclei take place in compounds that contain the elements fluorine and iodine, an intensive interaction does take place in compounds that contain fluorine and paramagnetic centers (radicals, metal ions), and said intensive interaction is expressed in a shortening of the relaxation time of the fluorine nucleus. The extent of this effect depends on the number of unpaired electrons of the metal ion ($Gd^{3+} > Mn^{2+} > Fe^{3+} > Cu^{2+}$) and on the removal between the paramagnetic ion and the $^{19}F$ atom.

The more unpaired electrons of the metal ion are present and the closer the latter are brought to the fluorine, the greater the shortening of the relaxation time of the fluorine nucleus.

The shortening of the relaxation time as a function of the interval from the paramagnetic ion becomes apparent in all nuclei with an uneven spin number, thus also in the case of protons, and gadolinium compounds are therefore widely used as contrast media in nuclear spin tomography (Magnevist®, Prohance®, Omniscan® and Dotarem®).

In $^1$H-MR imaging ($^1$H-MRI), however, relaxation time $T^1$ or $T^2$ of the protons, i.e., primarily the protons of water, and not the relaxation time of the fluorine nuclei is measured and used for the imaging. The quantitative measurement for the shortening of the relaxation time is the relaxivity [L/mmol·s]. To shorten the relaxation times, complexes of paramagnetic ions are successfully used. In the table below, the relaxivity of several commercial preparations is indicated:

|  | $T^1$ Relaxivity in Water [L/mmol · s, 39° C., 0.47 T] | $T^1$ Relaxivity in Plasma [L/mmol · s, 39° C., 0.47 T] |
|---|---|---|
| MAGNEVIST ® | 3.8 | 4.8 |
| DOTAREM ® | 3.5 | 4.3 |
| OMNISCAN ® | 3.8 | 4.4 |
| PRO HANCE ® | 3.7 | 4.9 |

In these compounds, only interactions between protons and the gadolinium ion take place. A relaxivity of about 4 [L/mmol·s] is thus observed for these contrast media in water.

Both fluorine compounds for fluorine-19 imaging, in which the shortened relaxation time of the fluorine nucleus is used, and non-fluorine-containing compounds, in which the relaxation time of the protons of water is measured, are thus used successfully for MR imaging.

In the introduction of a perfluorocarbon-containing radical in a paramagnetic contrast medium, i.e., in the combination of properties that were previously known to be suitable only for fluorine-imaging compounds, with compounds that were used for proton imaging, surprisingly enough, the relaxivity that relates to the protons of water also quickly increases. It now reaches values of 10-50 [L/mmol·s] in comparison to values of between 3.5 and 3.8 [L/mmol·s] as they were already cited for some commercial products in the table above.

Perfluoroalkyl-containing metal complexes are already known from DE 196 03 033.1, WO 99/01161, DE 19914101, DE 10040381, and DE 10040858. These compounds cannot be used satisfactorily, however, for all applications, since the compatibility is inadequate in most cases. Thus, there is still a need for MRT contrast media that both have excellent imaging properties and are at the same time excellently compatible in obtaining the non-invasive nature of the diagnostic method. This is important, for example, if tumors, including satellite metastases, are to be diagnosed and thus a distribution of the contrast medium over the entire body is to be achieved.

Malignant tumors metastasize in clusters in regional lymph nodes, whereby several lymph node stations can also be involved. Thus, lymph node metastases are found in about 50-69% of all patients with malignant tumors (Elke, Lymphographie [Lymphography], in: Frommhold, Stender, Thurn (Eds.), Radiologische Diagnostik in Klinik und Praxis [Radiological Diagnosis in Clinical Studies and in Practice], Volume IV, Thieme Verlag Stuttgart, $7^{th}$ Ed., 434-496, 1984). The diagnosis of a metastatic attack of lymph nodes is of great importance with respect to the therapy and prognosis of malignant diseases. With the modern imaging methods (CT, US and MRI), lymphogenous evacuations of malignant tumors are only inadequately detected, since in most cases, only the size of the lymph node can be used as a diagnostic criterion. Thus, small metastases in non-enlarged lymph nodes (<2 cm) cannot be distinguished from lymph node hyperplasias without a malignant attack (Steinkamp et al., Sonographie und Kernspintomographie: Differentialdiagnostik von reaktiver Lymphknoten-vergrößerung und Lymphknotenmetastasen am Hals [Sonography and Nuclear Spin Tomography: Differential Diagnosis of Reactive Lymph Node Enlargement and Lymph Node Metastases on the Neck], Radiol. Diagn. 33: 158, 1992).

It would be desirable that when using specific contrast media, lymph nodes with metastatic attack and hyperplastic lymph nodes can be distinguished.

The direct x-ray lymphography (injection of an oily contrast medium suspension in a prepared lymph vessel) is known as an invasive method, used only rarely, that can visualize only a few lymph drainage stations.

Fluorescence-labeled dextrans are also used experimentally in animal experiments to be able to observe the lymph drainage after their interstitial administration. After interstitial/intracutaneous administration, all commonly used markers for the visualization of lymph tracts and lymph nodes have in common the fact that they are substances with a particulate nature ("particulates," e.g., emulsions and nanocrystal suspensions) or large polymers (see above, WO 90/14846). The previously described preparations have proven to be still not optimally suitable for indirect lymphography, however, because of their deficient local and systemic compatibility as well as their small lymphatic passageway, which causes insufficient diagnostic efficiency.

Since the visualization of lymph nodes is of central importance for the early detection of metastatic attack in cancer patients, a great need for lymph-specific contrast medium preparations exists for diagnosis of corresponding changes of the lymphatic system, which are characterized by very good compatibility. In terms of this invention, the lymphatic system comprises both the lymph nodes and the lymph vessels. The substances of this invention are therefore suitable for diagnosis of changes of the lymphatic system, preferably for diagnosis of changes of the lymph nodes and/or the lymph vesels, in particular diagnoses of metastases in lymph nodes.

The highest possible contrast medium concentration and high stability are just as desirable as the diagnostically relevant, most uniform possible lymphatic concentration over several lymph stations. The burden on the overall organism should be kept low by quick and complete excretion of the contrast medium. A quick start-up, if possible as early as within a few hours after the administration of contrast medium, is important for radiological practice. Good compatibility is necessary.

Last but not least, it is desirable to have lymph-specific contrast media available that allow both the primary tumor and a possible lymph node metastasis to be visualized in a diagnostic session.

Another important area in medicine is the detecting, locating and monitoring of necroses or infarctions. Thus, the myocardial infarction is not a stationary process, but rather a dynamic process that extends over a prolonged period (weeks to months). The disease runs its course in about three phases, which are not strictly separated from one another but rather are overlapping. The first phase, the development of the myocardial infarction, comprises the 24 hours after infarction, in which the destruction progresses like a shock wave (wave front phenomenon) from the subendocardium to the myocardium. The second phase, the already existing infarction, comprises the stabilization of the area in which fiber formation (fibrosis) takes place as a healing process. The third phase, the healed infarction, begins after all destroyed tissue is replaced by fibrous scar tissue. During this period, an extensive restructuring takes place.

Up until now, no precise and reliable process has been known that enables the current phase of a myocardial infarction in a living patient to be diagnosed. To evaluate a myocardial infarction, it is of decisive importance to know how large the portion of tissue that is definitively lost in the infarction is and at what point the loss occurred, since the type of therapy depends on this knowledge.

Infarctions occur not only in the myocardium but also in other tissues, especially in the brain.

While the infarction can be healed to a certain extent, only the harmful sequelae for the rest of the organism can be prevented or at least moderated in the case of a necrosis, locally limited tissue death. Necroses can develop in multiple ways: by injuries, chemicals, oxygen deficiency, or by radiation. As in the case of infarction, the knowledge of scope and type of necrosis is important for further medical treatment.

Tests to improve the localization of infarctions and necroses by the use of contrast media in non-invasive processes such as scintigraphy or nuclear spin tomography were therefore already carried out earlier. In the literature, tests to use porphyrins for necrosis imaging occupy a large space. The results that are achieved, however, paint a contradictory picture. In addition, porphyrins tend to be deposited in the skin, which leads to a photosensitization.

Contrast media, not derived from the porphyrin skeleton, for necrosis and infarction imaging are described in DE 19744003 (Schering A G), DE 19744004 (Schering A G) and WO 99/17809 (EPIX). To date, however, there are still no compounds that can be used satisfactorily as contrast media in infarction and necrosis imaging and are characterized at the same time by excellent compatibility.

The same problem exists in the area of compounds that can be used to diagnose thrombi or arteriosclerotic plaque: there are no compounds that can be used satisfactorily as contrast media for visualizing thrombi or arteriosclerotic plaque and are characterized at the same time by excellent compatibility.

An object of the invention was therefore to make available contrast media that have, on the one hand, excellent imaging properties as MRT contrast media and are suitable in particular for tumor and necrosis imaging, and/or lymphography and/or blood-pool imaging and/or for visualizing thrombi or arteriosclerotic plaque, and at the same time are distinguished by excellent compatibility.

The object of the invention is achieved by the perfluoroalkyl-containing complexes with a nitrogen-containing linker structure of general formula I

in which
R either represents
a monosaccharide or oligosaccharide radical that is bonded via the 1 —OH, in which case Q has the meaning of a group selected from:

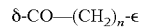

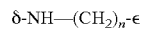

whereby
n" is an integer from 1 and 5, and
m is an integer from 1 and 6, and
whereby δ indicates the binding site to linker L, and ε represents the binding site to radical R;
or
R has one of the following meanings, then Q has the meaning of a direct bond: R means a polar radical that is selected from
The complexes K of general formulas II to V, whereby $R^1$ here means a hydrogen atom or a metal ion equivalent of the atomic numbers 20-29, 31-33, 37-39, 42-44, 49 or 57-83, and radicals $R^2$, $R^3$, $R^4$, U and $U^1$ have the meaning indicated below, or A carbon chain with 1-30 C atoms that is bonded via —CO—, —$NR^7$— or a direct bond to linker L, which can be straight or branched, saturated or unsaturated, and which optionally is interrupted by 1-10 oxygen atoms, 1-5 —NHCO groups, 1-5 —CONH groups, 1-2 sulfur atoms, 1-5 —NH groups or 1-2 phenylene groups, which optionally can be substituted by 1-2 OH groups, 1-2 $NH_2$ groups, 1-2 —COOH groups, or 1-2—$SO_3H$ groups, and which optionally is substituted by 1-10 —OH groups, 1-5 —COOH groups, 1-2 $SO_3H$ groups, 1-5 $NH_2$ groups, or 1-5 $C_1$-$C_4$-alkoxy groups, whereby $R^7$ means H or $C_1$-$C_4$-alkyl, $R_f$ is a perfluorinated, straight-chain or branched carbon chain with the formula —$C_nF_{2n}E$, in which E represents a terminal fluorine, chlorine, bromine, iodine or hydrogen atom, and n stands for the numbers 4-30, K stands for a metal complex of general formula II,

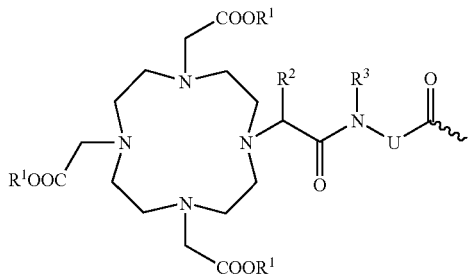

(II)

in which $R^1$ means a hydrogen atom or a metal ion equivalent of atomic numbers 21-29, 31-33, 37-39, 42-44, 49 or 57-83, provided that at least two $R^1$ stand for metal ion equivalents, $R^2$ and $R^3$, independently of one another, represent hydrogen, $C_1$-$C_7$-alkyl, benzyl, phenyl, —$CH_2OH$ or —$CH_2OCH_3$, and U stands for —$C_6H_4$—O—$CH_2$-ω-, —$(CH_2)_{1-5}$-ω, a phenylene group, a —$CH_2$—NHCO—$CH_2$—CH ($CH_2COOH$)—$C_6H_4$-ω-, —$C_6H_4$—$(OCH_2CH_2)_{0-1}$—N($CH_2COOH$)—$CH_2$-ω or a $C_1$-$C_{12}$-alkylene or —$(CH_2)_{7-12}$—$C_6H_4$—O group that optionally is interrupted by one or more oxygen atoms, 1 to 3 —NHCO groups, or 1 to 3 —CONH groups and/or is substituted by 1 to 3 —$(CH_2)_{0-5}COOH$ groups, whereby ω stands for the binding site to —CO—, or of general formula III

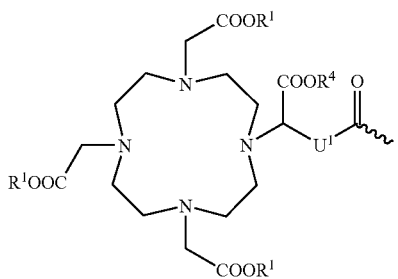

(III)

in which $R^1$ has the above-mentioned meaning, $R^4$ represents hydrogen or a metal ion equivalent that is mentioned under $R^1$, and $U^1$ represents —$C_6H_4$—O—$CH_2$-ω- or a group —$(CH_2)_p$—, whereby ω means the binding site to —CO— and $p^1$ is an integer between 1 and 4, or of general formula IV

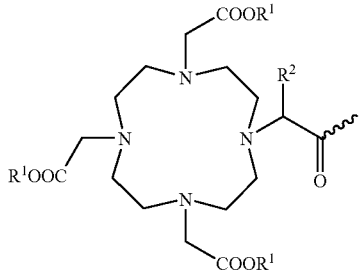

(IV)

in which $R^1$ and $R^2$ have the above-mentioned meaning or of general formula V A or V B

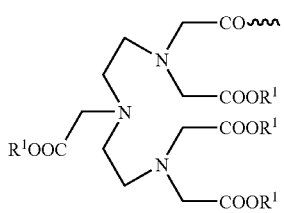

(V A)

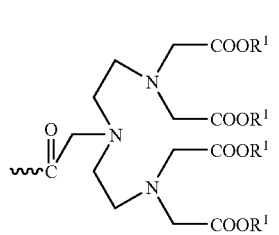

(V B)

in which $R^1$ has the above-mentioned meaning, or of general formula VI

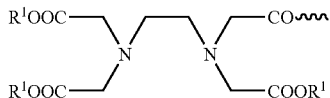

(VI)

in which R¹ has the above-mentioned meaning, or of general formula VII

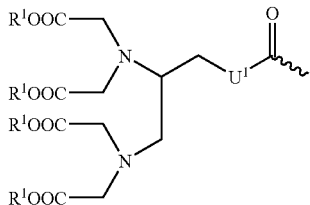

(VII)

in which R¹ and U1 have the above-mentioned meaning, whereby ω means the binding site to —CO—, or of general formula VIII

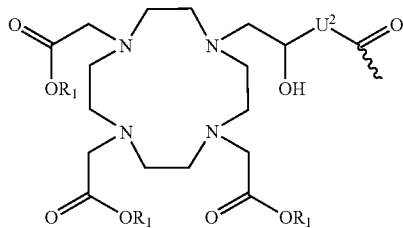

(VIII)

in which R¹ has the above-mentioned meaning, and U² represents a straight-chain or branched, saturated or unsaturated $C_1$-$C_{20}$ alkylene group that optionally contains imino, phenylene, phenylenoxy, phenylenimino, amide, hydrazide, carbonyl, ester groups, oxygen, sulfur and/or nitrogen atom(s) and that optionally is substituted by hydroxy, mercapto, oxo, thioxo, carboxy, carboxyalkyl, ester and/or amino group(s), and free acid groups, optionally present in radical K, can optionally be present as salts of organic and/or inorganic bases or amino acids or amino acid amides, and L represents a radical that is selected from radicals IXa) to IXc) below:

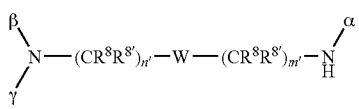

(IXa)

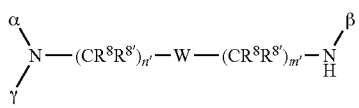

(IXb)

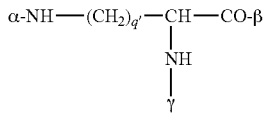

(IXc)

whereby n' and m', independently of one another, represent an integer between 0 and 4, and m'+n'≧1; preferably m'+n' is equal to 1, 2, or 3, and $R^8$ and $R^{8'}$, independently of one another, are either —H or —OH, whereby with m'+n'>1, each group —($CR^8R^{8'}$)— can be different, and W is either a direct bond, —O— or a phenylene group, which optionally can be substituted by 1 to 4 hydroxy groups, and q' is either 1, 2, 3 or 4, whereby α means the binding site of L to complex K, β is the binding site of L to radical Q, and γ represents the binding site of L to radical X, and X stands for a group of formula (VI)

$$\rho\text{-Y}-(CH_2)_s\text{-}(G)_t\text{-}(CH_2)_{s'}\text{-}\zeta \quad \quad (X)$$

whereby Y means a direct bond, a group —CO— or a group $NR^6$, whereby $R^6$ stands for —H or a straight or branched, saturated or unsaturated $C_1$-$C_{15}$ carbon chain, which can be interrupted by 1-4 O atoms, 1-3 —NHCO groups, 1-3 —CONH groups, 1-2 —$SO_2$ groups, 1-2 sulfur atoms, 1-3 —NH groups or 1-2 phenylene groups, which optionally can be substituted by 1-2 OH groups, 1-2 $NH_2$ groups, 1-2 —COOH groups or 1-2 —$SO_3H$ groups, and which optionally is substituted by 1-10 OH groups, 1-5 —COOH groups, 1-2 —$SO_3H$ groups, 1-5 $NH_2$ groups, or 1-5 $C_1$-$C_4$-alkoxy groups, and G means either —O— or —$SO_2$—, s and s', independently of one another, mean either 1 or 2, t means either 0 or 1, and ρ represents the binding site of X to L and ζ represents the binding site of X to $R_f$.

In a preferred embodiment, $R^6$ is H or a $C_1$-$C_6$-alkyl group, which can be interrupted by 1-3 O atoms and which can be substituted by 1-4 —OH groups.

In an especially preferred embodiment, $R^6$ is a $C_1$-$C_4$ alkyl group.

In a preferred embodiment, G means the group —O—.

In an especially preferred embodiment, t=0.

In a preferred embodiment, W is a direct bond.

In a preferred embodiment, radical R that is bonded to linker L via a —CO—, —$NR^7$— or a direct bond is a carbon chain with 1-30 C atoms that is interrupted by 1 to 10 oxygen atoms and/or is substituted by 1-10 OH groups.

In an especially preferred embodiment, R is a C1-C12 carbon chain that is bonded via a —CO—, —$NR^7$— or direct bond to L, which is interrupted by 1 to 6 oxygen atoms and/or is substituted by 1-6 OH groups.

If the compound according to the invention is intended for use in NMR diagnosis, the metal ion of the signaling group must be paramagnetic. These are in particular the divalent and trivalent ions of elements of atomic numbers 21-29, 42, 44 and 58-70. Suitable ions are, for example, the chromium(III), iron(II), cobalt (II), nickel(II), copper(II), praseodymium (III), neodymium(III), samarium(III) and ytterbium(III) ions.

Because of their strong magnetic moment, gadolinium(III), terbium(III), dysprosium(III), holmium(III), erbium(III), iron(III) and manganese(II) ions are especially preferred.

For use of the compounds according to the invention in nuclear medicine (radiodiagnosis and radiotherapy), the metal ion must be radioactive. For example, radioisotopes of elements with atomic numbers 27, 29, 31-33, 37-39, 43, 49, 62, 64, 70, 75 and 77 are suitable. Technetium, gallium, indium, rhenium and yttrium are preferred.

If the compound according to the invention is intended for use in x-ray diagnosis, the metal ion is preferably derived from an element of a higher atomic number to achieve sufficient absorption of x-rays. It was found that for this purpose, diagnostic agents that contain a physiologically compatible complex salt with metal ions of elements of atomic numbers 25, 26 and 39 as well as 57-83 are suitable.

Manganese(II), iron(II), iron(III), praseodymium(III), neodymium(III), samarium(III), gadolinium(III), ytterbium(III) or bismuth(III) ions, in particular dysprosium(III) ions and yttrium(III) ions, are preferred.

Acidic hydrogen atoms that are optionally present in $R^1$, i.e., those that have not been substituted by the central ion, can optionally be replaced completely or partially by cations of inorganic and/or organic bases or amino acids or amino acid amides.

Suitable inorganic cations are, for example, the lithium ion, the potassium ion, the calcium ion and in particular the sodium ion. Suitable cations of organic bases are, i.a., those of primary, secondary or tertiary amines, such as, for example, ethanolamine, diethanolamine, morpholine, glucamine, N,N-dimethylglucamine and in particular N-methylglucamine. Suitable cations of amino acids are, for example, those of lysine, arginine and ornithine as well as the amides of otherwise acidic or neutral amino acids.

Especially preferred compounds of general formula I are those with macrocyclic compound K of general formula II.

Radical U in metal complex K preferably means —$CH_2$— or $C_6H_4$—O—$CH_2$-ω, whereby ω stands for the binding site to —CO—.

In a preferred embodiment, $U^2$ is a $C_1$-$C_6$ alkylene chain, which optionally is interrupted by 1 to 2 —NHCO groups and/or 1 to 2 O atoms, and which can be substituted by 1 to 3 —OH groups.

Radical $U^2$ in metal complex K preferably means in particular:
  a linear alkylene group with 1 to 6 C atoms, in particular 2, 3 or 4 C atoms, or
  a linear alkylene group with 1 to 6 C atoms, in particular 2, 3 or 4 C atoms, which is interrupted by 1 O atom, or
  a linear alkylene group with 1 to 6 C atoms, in particular 2, 3 or 4 C atoms, which contains an —NHCO group.

In an especially preferred embodiment, $U^2$ is an ethylene group.

Alkyl groups $R^2$ and $R^3$ in the macrocyclic compound of general formula II can be straight-chain or branched. By way of example, methyl, ethyl, propyl, isopropyl, n-butyl, 1-methylpropyl, 2-methylpropyl, n-pentyl, 1-methylbutyl, 2-methylbutyl, 3-methylbutyl, and 1,2-dimethylpropyl can be mentioned. $R^2$ and $R^3$, independently of one another, preferably mean hydrogen or $C_1$-$C_4$-alkyl.

In a quite especially preferred embodiment, $R^2$ stands for methyl and $R^3$ stands for hydrogen.

The benzyl group or the phenyl group $R^2$ or $R^3$ in macrocyclic compound K of general formula II can also be substituted in a ring.

In another preferred embodiment of the invention, R means a monosaccharide radical with 5 or 6 C atoms, preferably glucose, mannose, galactose, ribose, arabinose or xylose or their deoxy sugar, such as, for example, 6-deoxygalactose (fucose) or 6-deoxymannose (rhamnose) or their peralkylated derivatives. Especially preferred are glucose, mannose and galactose, in particular mannose.

In another preferred embodiment of this invention, R is selected from one of the following radicals:

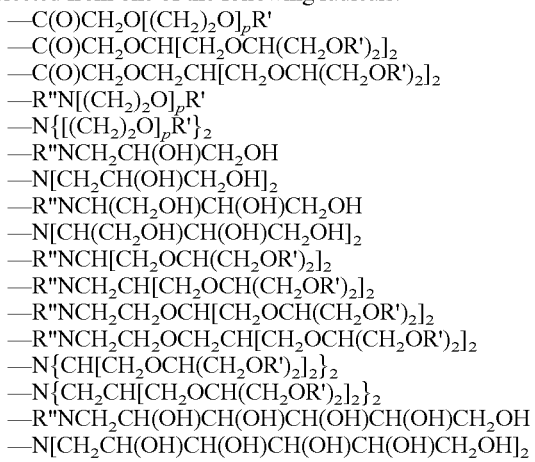

and a complex of formula (II), with Q in the meaning of a direct bond,
  whereby $R^1$, $R^2$, $R^3$ and U are defined as above for formula (II),
  p is either 1, 2, 3, 4, 5, 6, 7, 8 or 9,
  $R^1$ is either H or $CH_3$, and R" is either H or a $C_1$ to $C_4$-alkyl radical.
  p is preferably 1, 2, 3, or 4.

The polar radicals that are indicated here are commercially available products or are produced according to the methods that are described in the literature.
  Cassel et al., Eur. J. Org. Chem., 2001, 5, 875-896
  Whitessides et al., JACS, 1994, 5057-5062
  Voegtle et al., Liebigs Ann. Chem., 1980, 858-862
  Liu et al., Chem. Commun., 2002, 594
  Mitchell et al., Heterocyclic Chem., 1984, 697-699
  Bartsch et al., J. Org. Chem., 1984, 4076-4078
  Keana et al., J. Org. Chem., 1983, 2647-2654

In a quite especially preferred embodiment, R is a radical of formula: —C(O)$CH_2$O[($CH_2$)$_2$O]$_p$R' that is bonded via —CO— to L.

With p and R' in the above-indicated meaning, R' is especially preferably the group $CH_3$.

In another preferred embodiment, Q has the meaning of a group that is selected from:

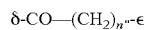

whereby
  n" is an integer from 1 and 5, and
  L at the same time has the meaning of a group of formula IXa or IXb.

In another preferred embodiment, Q has the meaning of a group that is selected from:

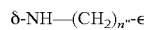

whereby
  n" is an integer from 1 and 5, and
  L at the same time has the meaning of a group IXc.

Of the compounds of general formula I according to the invention, in addition those are preferred in which $R_f$ means —$C_nF_{2n+1}$; i.e., E in the formula —$C_nF_{2n}$E means a fluorine atom. n preferably stands for the numbers 4-15. Quite especially preferred are the radicals —$C_4F_9$, —$C_6F_{13}$, —$C_8F_{17}$, —$C_{12}F_{25}$ and —$C_{14}F_{29}$ as well as the radicals of the compounds that are mentioned in the examples.

The nitrogen-containing radical L in general formula I, which represents the "skeleton," means the amino acid radical (Vc) in a preferred embodiment of the invention.

In another preferred embodiment, the nitrogen-containing radical L in general formula I represents a diamine radical of formula (IXb) or (IXa).

The perfluoroalkyl-containing metal complexes with a nitrogen-containing linker structure of general formula I

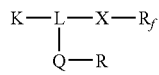
(I)

with K in the meaning of a metal complex of general formulas II to IV and L, Q,

X, R, and $R_f$ in the above-indicated meaning, are produced, in a way that is known in the art, by a carboxylic acid of general formula IIa

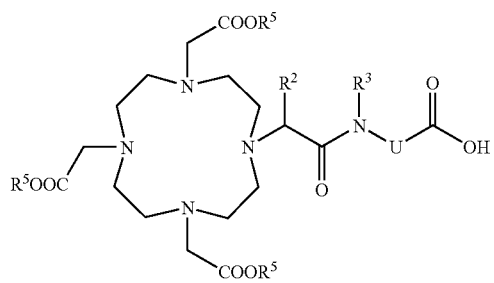
(IIa)

in which $R^5$ means a metal ion equivalent of atomic numbers 21-29, 31-33, 37-39, 42-44, 49 or 57-83 or a carboxyl protective group, and $R^2$, $R^3$ and U have the above-mentioned meaning, or a carboxylic acid of general formula IIIa

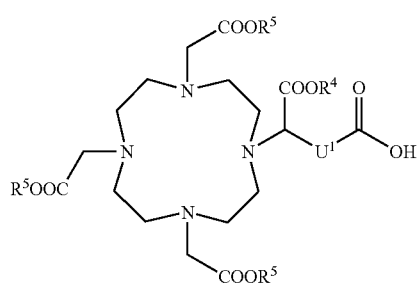
(IIIa)

in which $R^4$, $R^5$ and $U^1$ have the above-mentioned meaning, or a carboxylic acid of general formula IVa

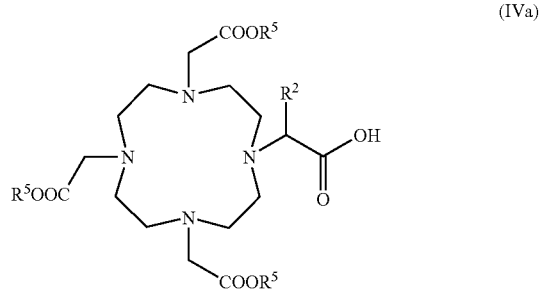
(IVa)

in which $R^5$ and $R^2$ have the above-mentioned meaning, or a carboxylic acid of general formula Va or Vb

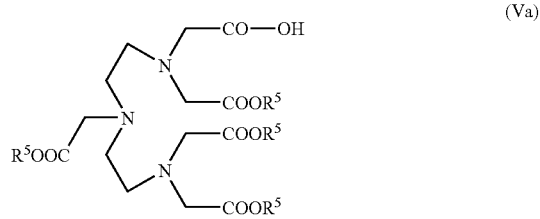
(Va)

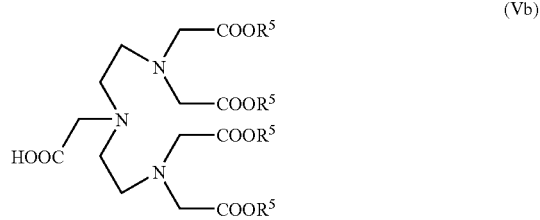
(Vb)

in which $R^5$ has the above-mentioned meaning, or a carboxylic acid of general formula VIa

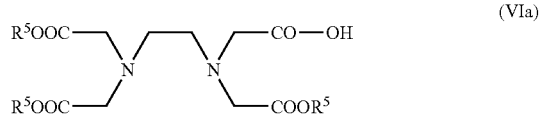
(VIa)

in which $R^5$ has the above-mentioned meaning, or a carboxylic acid of general formula VIIa

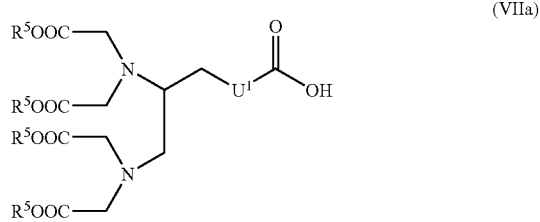
(VIIa)

in which $R^5$ and $U^1$ have the above-mentioned meanings,

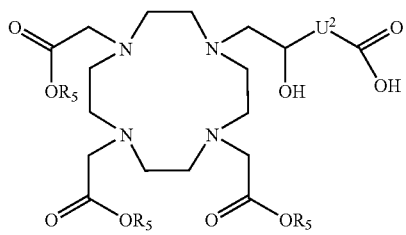
(VIIIa)

in which $R^5$ and $U^2$ have the above-mentioned meanings, being reacted in optionally activated form with an amine of general formula XI

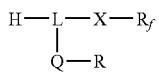
(XI)

in which L, R, $R_f$, Q and X have the above-indicated meaning, in a coupling reaction and optionally subsequent cleavage of optionally present protective groups to form a metal complex of general formula I
or
if $R^5$ has the meaning of a protective group, being reacted after cleavage of these protective groups in a subsequent step in a way that is known in the art with at least one metal oxide or metal salt of an element of atomic numbers 21-29, 31-33, 37-39, 42-44, 49 or 57-83, and then, if desired, optionally present acidic hydrogen atoms being substituted by cations of inorganic and/or organic bases, amino acids or amino acid amides.

This process for the production of metal complex carboxylic acid amides is known from DE 196 52 386.

The mixture that is used in the coupling reaction and that consists of metal complex carboxylic acid IIIb, which contains optionally present carboxy and/or hydroxy groups in protected form and at least one solubilizing substance in an amount up to 5, preferably 0.5-2 molar equivalents relative to the metal complex carboxylic acid, can both be produced in an upstream reaction stage and isolated (e.g., by concentration by evaporation, freeze-drying or spray-drying of an aqueous or water-miscible solution of the components or by precipitation with an organic solvent from such a solution) and then can be reacted in DMSO with dehydrating reagent and optionally a coupling adjuvant and can be formed by metal complex carboxylic acid, dehydrating reagent and optionally a coupling adjuvant in situ optionally by adding solubilizing substance(s) to the DMSO suspension.

The reaction solution that is produced according to one of these processes is held for pretreatment (acid activation) for 1 to 24, preferably 3 to 12 hours, at temperatures of 0 to 50° C., preferably at room temperature.

Then, an amine of general formula XI

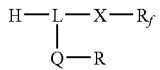
(XI)

in which radicals L, R, $R_f$, Q and X have the above-indicated meanings, is added without solvent or in dissolved form, for example in dimethyl sulfoxide, alcohols such as, e.g., methanol, ethanol, isopropanol or their mixtures, formamide, dimethylformamide, water or mixtures of the cited solvent, preferably in dimethyl sulfoxide, in water or in solvents that are mixed with water. For amide coupling, the thus obtained reaction solution is held at temperatures of 0 to 70° C., preferably 30 to 60° C., for 1 to 48 hours, preferably 8 to 24 hours.

In some cases, it has proven advantageous to use the amine in the form of its salts, e.g., as hydrobromide or hydrochloride in the reaction. To release the amine, a base, such as, e.g., triethylamine, diisopropylethylamine, N-methylmorpholine, pyridine, tripropylamine, tributylamine, lithium hydroxide, lithium carbonate, sodium hydroxide or sodium carbonate, is added.

The optionally still present protective groups are then cleaved off.

The isolation of the reaction product is carried out according to the methods that are known to one skilled in the art, preferably by precipitation with organic solvents, preferably acetone, 2-butanone, diethyl ether, ethyl acetate, methyl-t-butyl ether, isopropanol or their mixtures. Additional purification can be carried out by, for example, chromatography, crystallization or ultrafiltration.

As solubilizing substances, alkali salts, alkaline-earth salts, trialkylammonium salts, tetraalkylammonium salts, ureas, N-hydroxyimides, hydroxyaryl triazoles, substituted phenols and salts of heterocyclic amines are suitable. By way of example, there can be mentioned: lithium chloride, lithium bromide, lithium iodide, sodium bromide, sodium iodide, lithium methanesulfonate, sodium methane sulfonate, lithium-p-toluenesulfonate, sodium-p-toluene-sulfonate, potassium bromide, potassium iodide, sodium chloride, magnesium bromide, magnesium chloride, magnesium iodide, tetraethylammonium-p-toluenesulfonate, tetramethylammonium-p-toluenesulfonate, pyridinium-p-toluenesulfonate, triethylammonium-p-toluenesulfonate, 2-morpholinoethylsulfonic acid, 4-nitrophenol, 3,5-dinitrophenol, 2,4-dichlorophenol, N-hydroxysuccinimide, N-hydroxyphthalimide, urea, tetramethylurea, N-methylpyrrolidone, formamide as well as cyclic ureas, whereby the first five mentioned above are preferred.

As dehydrating reagents, all agents that are known to one skilled in the art are used. By way of example, carbodiimides and onium reagents, such as, e.g., dicyclohexylcarbodiimide (DCCI), 1-ethyl-3-(3-dimethylaminopropyl)-carbodiimide hydroxychloride (EDC), benzotriazol-1-yloxytris(dimethylamino)-phosphonium hexafluorophosphate (BOP) and O-(benzotriazol-1-yl)-1,1,3,3-tetramethyluronium hexafluorophosphate (HBTU), preferably DCCI, can be mentioned.

In literature, for example, the following suitable processes are described:

Aktivierung von Carbonsäuren. Übersicht in Houben-Weyl, Methoden der Organischen Chemie [Activation of Carboxylic Acids. Survey in Houben-Weyl, Methods of Organic Chemistry], Volume XV/2, Georg Thieme Verlag Stuttgart, 1974 (and J. Chem. Research (S) 1996, 302).

Aktivierung mit Carbodiimiden [Activation with Carbodiimides]. R. Schwyzer and H. Kappeler, Helv. 46: 1550 (1963).

E. Wünsch et al., Vol. 100: 173 (1967).

Aktivierung mit Carbodiimiden/Hydroxysuccinimid [Activation with Carbodiimides/Hydroxy Succinimide]: J. Am. Chem. Soc. 86: 1839 (1964) as well as J. Org. Chem. 53: 3583 (1988). Synthesis 453 (1972).

Anhydridmethode, 2-Ethoxy-1-ethoxycarbonyl-1,2-dihydrochinolin [Anhydride Method, 2-Ethoxy-1-ethoxycarbonyl-1,2-dihydroquinoline]: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).

Imidazolid-Methode [Imidazolide Method]: B. F. Gisin, R. B. Menifield, D. C. Tosteon, Am. Soc. 91: 2691 (1969).

Säurechlorid-Methoden, Thionylchlorid [Acid Chloride Methods, Thionyl Chloride]: Helv., 42: 1653 (1959).

Oxalylchlorid [Oxalyl Chloride]: J. Org. Chem., 29: 843 (1964).

As coupling adjuvants that are optionally to be used, all that are known to one skilled in the art are suitable (Houben-Weyl, Methoden der organischen Chemie, Volume XV/2, Georg Thieme-Verlag, Stuttgart, 1974). By way of example, there can be mentioned 4-nitrophenol, N-hydroxysuccinimide, 1-hydroxybenzotriazole, 1-hydroxy-7-aza-benzotriazole, 3,5-dinitrophenol and pentafluorophenol. Preferred are 4-nitrophenol and N-hydroxysuccinimide; especially preferred in this case is the first-mentioned reagent.

The cleavage of the protective groups is carried out according to the processes that are known to one skilled in the art, for example by hydrolysis, hydrogenolysis, alkaline saponification of esters with alkali in aqueous-alcoholic solution at temperatures of 0° to 50° C., acidic saponification with mineral acids or in the case of, e.g., tert-butyl esters with the aid of trifluoroacetic acid [Protective Groups in Organic Synthesis, $2^{nd}$ Edition, T. W. Greene and P. G. M. Wuts, John Wiley and Sons, Inc. New York, 1991], in the case of benzyl ethers with hydrogen/palladium/carbon.

The carboxylic acids of general formulas IIa to VIIa that are used are either known compounds or are produced according to processes that are described in the examples, see DE 10040381 and DE 10040858. Thus, the production of carboxylic acids of general formula IIa is known from DE 196 52 386. The carboxylic acids of general formula VIIIa that are used are produced as described in WO 95/17451.

The perbenzylated sugar acids that are used as starting substances when R is a mono- or oligosaccharide can be produced analogously to Lockhoff, Angew. Chem. [Applied Chem.] 1998, 110 No. 24, p. 3634 ff. Thus, e.g., the production of 1-O-acetic acid from perbenzyl glucose is carried out over 2 stages, via trichloroacetimidate and reaction with hydroxyacetic acid ethyl ester, $BF_3$ catalysis in THF and subsequent saponification with NaOH in MeOH/THF.

In a more advantageous process, as described in DE 10040381, the perbenzylated sugar acids that are used as starting substances can also be produced by the perbenzylated 1—OH sugars being dissolved in an organic solvent that is not water-miscible and being reacted with an alkylating reagent of general formula XI Nu-L-COO—SG    (XVIII), in which Nu means a nucleofuge, L is —$(CH_2)$—$_n$, (whereby n=1-5), —$CH_2$—CHOH—
or —CH(CHOH—$CH_2$OH)—CHOH—CHOH—, and Sg represents a protective group, in the presence of a base and optionally a phase transfer catalyst. As a nucleofuge, for example, the radicals —Cl, —Br, -J, —OTs, —OMs, —$OSO_2CF_3$, —$OSO_2C_4F_9$ or —$OSO_2C_8F_{17}$ can be contained in the alkylating reagent of general formula XVIII.

The protective group is a common acid protective group. These protective groups are well known to one skilled in the art (Protective Groups in Organic Syntheses, Second Edition, T. W. Greene and P. G. M. Wuts, John Wiley & Sons, Inc., New York 1991).

The reaction according to the invention can be carried out at temperatures of 0-50° C., preferably 0° C. to room temperature. The reaction times are from 10 minutes to 24 hours, preferably 20 minutes to 12 hours.

The base is added either in solid form, preferably in fine powder form, or as 10-70%, preferably 30-50%, aqueous solution. As preferred bases, NaOH and KOH are used.

As an organic, non-water-miscible solvent, for example, toluene, benzene, $CF_3$-benzene, hexane, cyclohexane, diethyl ether, tetrahydrofuran, dichloromethane, MTB or mixtures thereof can be used in the alkylating process according to the invention.

The quaternary ammonium or phosphonium salts that are known for this purpose or else crown ethers, such as, e.g., [15]-crown-5 or [18]-crown-6, are used as phase transfer catalysts in the process according to the invention. Quaternary ammonium salts with four identical or different hydrocarbon groups on the cation, selected from methyl, ethyl, propyl, isopropyl, butyl or isobutyl, are preferably suitable. The hydrocarbon groups on the cation must be large enough to ensure good solubility of the alkylating reagent in the organic solvent. $N(Butyl)_4^+$-$Cl^-$, $N(butyl)_4^+$-$HSO_4^-$, but also $N(methyl)_4^+$-$Cl^-$ are especially preferably used according to the invention.

The corresponding terminally protected polyethylene glycolic acids can also be produced analogously.

Compounds of general formula (XI)

with L in the meaning of

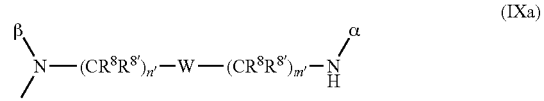

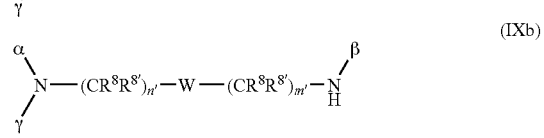

are produced by the above-described hydrophilic carboxylic acids R being reacted according to the methods of amide formation known to one skilled in the art with amines of general formula (XII)

with Sg in the meaning of a protective group and L, X and Rf in the above-indicated meaning.

The cleavage of the protective groups is carried out according to the processes that are known to one skilled in the art, for example by hydrolysis, hydrogenolysis, alkaline saponification of esters with alkali in aqueous-alcoholic solution at temperatures of 0° to 50° C., acidic saponification with mineral acids or in the case of, e.g., tert-butyl esters with the aid of trifluoroacetic acid [Protective Groups in Organic Synthesis, $2^{nd}$ Edition, T. W. Greene and P. G. M. Wuts, John Wiley and Sons, Inc. New York, 1991], in the case of benzyl ethers with hydrogen/palladiumn/carbon.

Compounds of general formula (XII) are produced by monoprotected diamines of general formula (XIII)

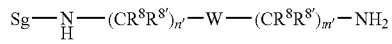 (XIII)

being reacted with $R^8$, $R^{8'}$, n', W and m' in the above-indicated meaning and with Sg in the meaning of a protective group with perfluorine-containing nucleophiles of general formula (XIV)

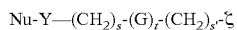 (XIV)

with Y, G, s, s' and ζ in the above-indicated meaning, in which Nu means a nucleofuge, in the presence of a base and optionally a phase transfer catalyst. As a nucleofuge, for example, the radicals —Cl, —Br, -J, —OTs, —OMs, —$OSO_2CF_3$, —$OSO_2C_4F_9$ or —$OSO_2C_8F_{17}$ can be contained in the alkylating reagent of general formula XVIII.

Known perfluorine-containing nucleophiles of general formula (XIV) as well as additional perfluoroalkyl-containing substances and their production are described in the following publications:

J. G. Riess, Journal of Drug Targeting, 1994, Vol. 2, pp. 455-468;

J. B. Nivet et al., Eur. J. Med. Chem., 1991, Vol. 26, pp. 953-960;

M.-P. Krafft et al., Angew. Chem., 1994, Vol. 106, No. 10, pp. 1146-1148;

M. Lanier et al., Tetrahedron Letters, 1995, Vol. 36, No. 14, pp. 2491-2492;

F. Guillod et al., Carbohydrate Research, 1994, Vol. 261, pp. 37-55;

S. Achilefu et al., Journal of Fluorine Chemistry, 1995, Vol. 70, pp. 19-26;

L. Clary et al., Tetrahedron, 1995, Vol. 51, No. 47, pp. 13073-13088;

F. Szoni et al., Journal of Fluorine Chemistry, 1989, Vol. 42, pp. 59-68;

H. Wu et al., Supramolecular Chemistry, 1994, Vol. 3, pp. 175-180;

F. Guileri et al., Angew. Chem. 1994, Vol. 106, No. 14, pp. 1583-1585;

M.-P. Krafft et al., Eur. J. Med. Chem., 1991, Vol. 26, pp. 545-550;

J. Greiner et al., Journal of Fluorine Chemistry, 1992, Vol. 56, pp. 285-293;

A. Milius et al., Carbohydrate Research, 1992, Vol. 229, pp. 323-336;

J. Riess et al., Colloids and Surfaces A, 1994, Vol. 84, pp. 33-48;

G. Merhi et al., J. Med. Chem., 1996, Vol. 39, pp. 4483-4488;

V. Cirkva et al., Journal of Fluorine Chemistry, 1997, Vol. 83, pp. 151-158;

A. Ould Amanetoullah et al., Journal of Fluorine Chemistry, 1997, Vol. 84, pp. 149-153;

J. Chen et al., Inorg. Chem., 1996, Vol. 35, pp. 1590-161;

L. Clary et al., Tetrahedron Letters, 1995, Vol. 36, No. 4, pp. 539-542;

M. M. Chaabouni et al., Journal of Fluorine Chemistry, 1990, Vol. 46, pp. 307-315;

A. Milius et al., New J. Chem., 1991, Vol. 15, pp. 337-344;

M.-P. Krafft et al., New J. Chem., 1990, Vol. 14, pp. 869-875;

J.-B. Nivet et al., New J. Chem., 1994, Vol. 18, pp. 861-869;

C. Santaella et al., New J. Chem., 1991, Vol. 15, pp. 685-692;

C. Santaella et al, New J. Chem., 1992, Vol. 16, pp. 399-404;

A. Milius et al., New J. Chem., 1992, Vol. 16, pp. 771-773;

F. Szönyi et al., Journal of Fluorine Chemistry, 1991, Vol. 55, pp. 85-92;

C. Santaella et al., Angew. Chem., 1991, Vol. 103, No. 5, pp. 584-586;

M.-P. Krafft et al., Angew. Chem., 1993, Vol. 105, No. 5, pp. 783-785;

EP 0 548 096 B1.

Compounds of general formula (XI) with L in the meaning of

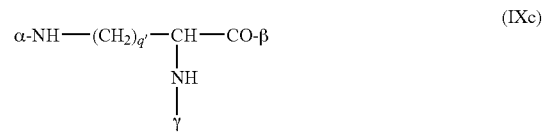 (IXc)

with q, α, β and γ in the above-indicated meaning, are produced by perfluorine-containing carboxylic acids of general formula (XV)

 (XV)

being reacted with X and $R_f$ in the above-indicated meaning, according to methods of amide formation, known to one skilled in the art, with amines of general formula (XVI)

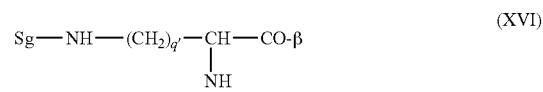 (XVI)

with q, β in the above-indicated meaning and with Sg in the meaning of a protective group.

The cleavage of the protective groups is carried out according to the processes that are known to one skilled in the art, for example by hydrolysis, hydrogenolysis, alkaline saponification of esters with alkali in aqueous-alcoholic solution at temperatures of 0° to 50° C., acidic saponification with mineral acids or in the case of, e.g., tert-butyl esters with the aid of trifluoroacetic acid [Protective Groups in Organic Synthesis, $2^{nd}$ Edition, T. W. Greene and P. G. M. Wuts, John Wiley and Sons, Inc., New York, 1991], in the case of benzyl ethers with hydrogen/palladium/carbon.

The production of compounds of general formula (XV) are described in the above-indicated literature citations for the production of perfluorine-containing compounds.

Compounds of general formula (XVI)

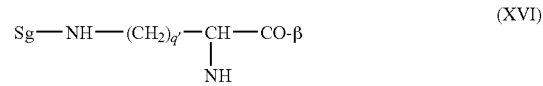 (XVI)

with q, β in the above-indicated meaning and with Sg in the meaning of a protective group are produced by the above-described hydrophilic amine R being reacted according to the methods of amide formation, known to one skilled in the art, with carboxylic acids of general formula (XVII)

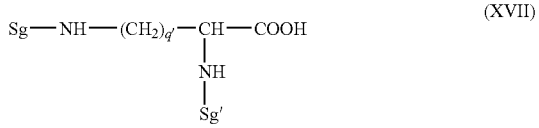

(XVII)

with q in the above-indicated meaning and with Sg and Sg' in the meaning of a protective group, whereby Sg and Sg' can be cleaved in different ways.

The cleavage of the protective groups is carried out according to the processes that are known to one skilled in the art, for example by hydrolysis, hydrogenolysis, alkaline saponification of esters with alkali in aqueous-alcoholic solution at temperatures of 0° to 50° C., acidic saponification with mineral acids or in the case of, e.g., tert-butyl esters with the aid of trifluoroacetic acid [Protective Groups in Organic Synthesis, $2^{nd}$ Edition, T. W. Greene and P. G. M. Wuts, John Wiley and Sons, Inc. New York, 1991], in the case of benzyl ethers with hydrogen/palladium/carbon.

Such 2x-protected amino acids of general formula (XVII) are commercially available products (Bachem).

The compounds according to the invention are especially suitable for use in NMR and x-ray diagnosis, radiodiagnosis and radiotherapy, as well as in MRT lymphography and in blood pool imaging. The perfluoroalkyl-containing metal complexes are especially suitable for use in nuclear spin resonance tomography (MRT) for visualizing various physiological and pathophysiological structures and thus for improving diagnostic information, for example the location and the extent of the disease, for selection and monitoring of the success of a targeted therapy and for prophylaxis of diseases and disorders.

In one especially preferred embodiment, the substances according to the invention are used for MRT lymphography.

In another especially preferred embodiment, the substances according to the invention are used for blood-pool imaging.

Suitable diseases and disorders comprise tumor diseases, especially detection and characterization of primary tumors, satellite metastases, lymph node metastases as well as necroses, cardiovascular diseases, especially changes in vessel diameter such as stenoses and aneurisms, arteriosclerosis by detection of arteriosclerotic plaque, thromboembolic diseases, infarctions, necroses, inflammations, especially arthritis, osteomyelitis, colitis ulcerosa, as well as nerve damage.

In an especially preferred embodiment, the substances according to the invention are used for necrosis or tumor imaging.

Subjects of the invention are also pharmaceutical agents that contain at least one physiologically compatible compound according to the invention, optionally with the additives that are commonly used in galenicals.

The compounds of this invention are distinguished by excellent compatibility and at the same time excellent imaging properties. They are thus especially well suited for systemic use in MRT, especially in MRT lymphography and in tumor imaging.

The production of the pharmaceutical agents according to the invention is carried out in a way that is known in the art, by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additions of complexing agents or weak complexes (such as, for example, diethylenetriaminepentaacetic acid or the Ca complexes that correspond to the metal complexes according to the invention) or—if necessary—electrolytes, such as, for example, sodium chloride or—if necessary—antioxidants, such as, for example, ascorbic acid.

If suspensions or solutions of the agents according to the invention in water or physiological salt solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention without isolating the complexes. In any case, special care must be used to perform the chelation so that the complexes according to the invention are virtually free of non-complexed metal ions that have a toxic action.

This can be ensured, for example, with the help of color indicators, such as xylenol orange, by control titrations during the production process. The invention therefore also relates to processes for the production of complex compounds and salts thereof. As a final precaution, there remains purification of the isolated complex.

In the in-vivo administration of the agents according to the invention, the latter can be administered together with a suitable vehicle, such as, for example, serum or physiological common salt solution, and together with another protein, such as, for example, human serum albumin (HSA).

The agents according to the invention are usually administered parenterally, preferably i.v. They can also be administered intravascularly or interstitially/intracutaneously depending on whether bodily vessels or tissue is/are to be examined.

The pharmaceutical agents according to the invention preferably contain 0.1 μmol-2 mol/l of the complex and are generally dosed in amounts of 0.001-5 mmol/kg.

The agents according to the invention fulfill the many requirements for suitability as contrast media for nuclear spin tomography. After oral or parenteral administration, they are thus extremely well suited for enhancing the informational value of the image that is obtained with the aid of a nuclear spin tomograph by increasing the signal intensity. They also show the great effectiveness that is necessary to load the body with the smallest possible amounts of foreign substances and the good compatibility that is necessary to maintain the non-invasive nature of the studies.

The good water solubility and low osmolality of the agents according to the invention allow the production of highly concentrated solutions to keep the volume burden of the circulatory system within reasonable limits and to offset the dilution by bodily fluid. In addition, the agents according to the invention show not only high stability in vitro but also surprisingly high stability in vivo, such that a release or an exchange of the ions, which are inherently toxic and bonded in the complexes, is carried out only extremely slowly within the time in which the new contrast media are completely excreted again.

In general, the agents according to the invention are dosed for use as NMR diagnostic agents in amounts of 0.0001-5 mmol/kg, preferably 0.005-0.5 mmol/kg.

The complex compounds according to the invention can also be used advantageously as susceptibility reagents and as shift reagents for in-vivo NMR spectroscopy.

Owing to their advantageous radioactive properties and the good stability of the complex compounds contained in them, the agents according to the invention are also suitable as radiodiagnostic agents. Details of such use and dosage are described in, e.g., "Radiotracers for Medical Applications," CRC Press, Boca Raton, Fla.

The compounds and agents according to the invention can also be used in positron-emission tomography, which uses positron-emitting isotopes such as, e.g.,$^{43}$Sc, $^{44}$Sc, $^{52}$Fe, $^{55}$Co, $^{68}$Ga, and $^{86}$Y (Heiss, W. D.; Phelps, M. E.; Positron Emission Tomography of Brain, Springer Verlag Berlin, Heidelberg, N.Y. 1983).

Histological studies confirm a regional microvascular hyperpermeability.

The contrast media according to the invention can therefore also be used for visualizing abnormal capillary permeability.

The compounds according to the invention are primarily distinguished in that they are completely eliminated from the body and thus are well tolerated. Thus, the excellent imaging properties can be used, and the non-invasive nature of the diagnosis is maintained.

Since the substances according to the invention accumulate in malignant tumors (no diffusion in healthy tissue, but high permeability of tumor vessels), they can also support the radiation therapy of malignant tumors. The latter is distinguished from the corresponding diagnosis only by the amount and type of the isotope that is used. The purpose in this case is the destruction of tumor cells by high-energy short-wave radiation with the smallest possible range of action. For this purpose, interactions of the metals that are contained in the complexes (such as, e.g., iron or gadolinium) with ionizing radiations (e.g., x-rays) or with neutron rays are used. By this effect, the local radiation dose at the site where the metal complex is found (e.g., in tumors) is significantly increased. To produce the same radiation dose in malignant tissue, the radiation exposure for healthy tissue can be considerably reduced and thus burdensome side effects for the patients can be avoided when such metal complexes are used. The metal complex conjugates according to the invention are therefore also suitable as radio-sensitizing substances in the radiation therapy of malignant tumors (e.g., use of Mössbauer effects or in the case of neutron capture therapy). Suitable β-emitting ions are, for example, $^{46}$Sc, $^{47}$Sc, $^{48}$Sc, $^{72}$Ga, $^{73}$Ga and $^{90}$Y. α-Emitting ions that exhibit suitable low half-lives are, for example, $^{211}$Bi, $^{212}$Bi, $^{213}$Bi, and $^{214}$Bi, whereby $^{212}$Bi is preferred. A suitable photon- and electron-emitting ion is $^{158}$Gd, which can be obtained from $^{157}$Gd by neutron capture.

If the agent according to the invention is intended for use in the variant of radiation therapy that is proposed by R. L. Mills et al. [Nature Vol. 336, (1988), p. 787], the central ion must be derived from a Mößbauer isotope, such as, for example, $^{57}$Fe or $^{151}$Eu.

In the in-vivo administration of the agents according to the invention, the latter can be administered together with a suitable vehicle, such as, for example, serum or physiological common salt solution, and together with another protein, such as, for example, human serum albumin. The dosage in this case depends on the type of cellular disruption, the metal ion that is used and the type of imaging method.

The agents according to the invention are usually administered parenterally, preferably i.v. They can also—as already discussed—be administered intravascularly or interstitially/intracutaneously depending on whether bodily vessels or tissue is/are to be examined.

The agents according to the invention are extremely well suited as x-ray contrast media, whereby it is especially to be emphasized that with them, no signs of the anaphylaxis-like reactions that are known from the iodine-containing contrast media can be detected in biochemical-pharmacological studies. They are especially valuable owing to the advantageous absorption properties in ranges of higher tube voltages for digital subtraction techniques.

In general, the agents according to the invention are dosed for use as x-ray contrast media analogously to, for example, meglumine-diatrizoate in amounts of 0.1-5 mmol/kg, preferably 0.25-1 mmol/kg.

The term "metal ion equivalent," as used in the application, is a common term, known to one skilled in the art, in the area of complex chemistry. A metal ion equivalent is an equivalent to metal ions, which can bind to, e.g., a carboxylate group instead of hydrogen. For example, a $Gd^{3+}$ can bind to 3 carboxylate groups, i.e., ⅓ $Gd^{3+}$ corresponds to the metal ion equivalent $R^1$ in formula (II), (III), (IV) or (V) if the metal is gadolinium.

BRIEF DESCRIPTION OF DRAWINGS

FIG. 5 shows images of popliteal lymph nodes using the compounds of Examples 5c, 14c and 15c.

EXAMPLES

Figure 1:
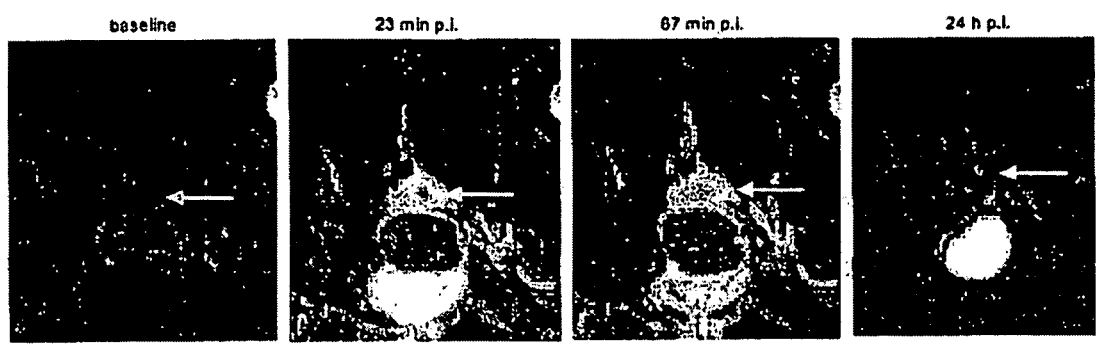
FIGS. 1 and 2 show lymph node images using the compound of Example 1d.

Example 1 a) 1-N-(Benzyloxycarbonyl)-1H,1H,2H,2H,4H,4H, 5H,5H-3-aza-perfluorotridecylamine 23.31 g (120 mmol) of N-benzyloxycarbonyl-ethylenediamine (Atwell et al., *Synthesis,* 1984, 1032-1033) and 10.2 g (100 mmol) of triethylamine are added to 54.22 g (100 mmol) of methanesulfonic acid-(1H,1H,2H,2H-perfluorodecyl)-ester (Bartsch et al., *Tetrahedron,* 2000, 3291-3302) in 500 ml of acetonitrile, and it is stirred for 48 hours at 60° C. Insoluble components are filtered out from the reaction solution, it is evaporated to the dry state in a vacuum, and the residue is chromatographed on silica gel (mobile solvent: dichloromethane/methanol 20:1).

| Yield: 32.8 g (51% of theory) of a colorless wax | | | | |
|---|---|---|---|---|
| Elementary Analysis: | | | | |
| Cld.: | C 37.51 | H 2.68 | N 4.37 | F 50.44 |
| Fnd.: | C 37.82 | H 2.74 | N 4.29 | F 50.27 | b) N-[2-(Benzyloxycarbonyl)-aminoethyl-N-(1H,1H, 2H,2H-perfluorodecyl)-2-[1-O-α-d-(2,3,4,6-tetra-O-benzyl)mannopyranosyl]-acetamide 8.05 g (39.04 mmol) of dicyclohexylcarbodiimide is added at 0° C. to a solution of 20 g (31.23 mmol) of the title compound of Example 1a and 18.70 g (31.23 mmol) of 1-O-α-d-carbonylmethyl-(2,3,4,6-tetra-O-benzyl)mannopyranose (produced according to WO 99/01160 A1) and 3.59 g (31.23 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20: 1).

Yield: 29.8 g (78% of theory) of a colorless, viscous oil.
Elementary Analysis:

| | | | | |
|---|---|---|---|---|
| Cld.: | C 55.09 | H 4.38 | N 2.29 | F 26.45 |
| Fnd.: | C 55.27 | H 4.40 | N 2.24 | F 26.31 | c) N-(2-Aminoethyl)-N-(1H,1H,2H,2H-perfluorodecyl)-2-(1-O-α-d-mannopyranosyl)-acetamide, Methanesulfonic Acid Salt 2.29 g (23.75 mmol) of the methanesulfonic acid as well as 4.0 g of palladium catalyst (10% Pd/C) are added to a solution of 29 g (23.75 mmol) of the title compound of Example 1b in 500 ml of ethanol, and it is hydrogenated for 24 hours at room temperature. Catalyst is filtered out, and the filtrate is evaporated to the dry state in a vacuum.

Yield: 19.5 g (quantitative) of a colorless solid.
Elementary Analysis:

| | | | | |
|---|---|---|---|---|
| Cld.: | C 30.67 | H 3.31 | N 3.41 | F 39.27 |
| Fnd.: | C 31.01 | H 3.29 | N 3.33 | F 39.04 | d) N-{[1,4,7-Tris-(carboxylatomethyl)-1,4,7,10-tetracyclododecane-10-N-(pentanoyl-3-aza-4-oxo-5-methyl-5-yl)]-2-aminoethyl}-N-(1H,1H,2H,2H-perfluorodecyl)-2-(1-O-α-d-mannopyranosyl)-acetamide, Gd Complex 18.7 g (22.72 mmol) of the title compound of Example 1c, 2.61 g (22.72 mmol) of N-hydroxysuccinimide, 1.93 g (45.44 mmol) of lithium chloride and 14.31 g (22.72 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 5.86 g (28.4 mmol) of dicyclohexyl carbodiimide as well as 2.30 g (22.72 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 22.3 g (68% of theory) of a colorless solid
Water content (Karl-Fischer): 7.0%
Elementary Analysis (relative to the anhydrous substance):

| | | | | | |
|---|---|---|---|---|---|
| Cld.: | C 35.01 | H 3.84 | N 7.33 | F 24.14 | Gd 11.75 |
| Fnd.: | C 35.21 | H 3.89 | N 7.27 | F 24.09 | Gd 11.61 |

Example 2 a) 1-N-(Benzyloxycarbonyl)-1H,1H,2H,2H,4H,4H, 5H,5H-3-N-[1,4,7-tris-(carboxylatomethyl)-1,4,7,10-tetraazacyclododecane-10-N-(pentanoyl-3-aza-4-oxo-5-methyl-5-yl)]-perfluorotridecylamine, Gd Complex 10.0 g (15.62 mmol) of the title compound of Example 1a, 1.80 g (15.62 mmol) of N-hydroxysuccinimide, 1.33 g (31.34 mmol) of lithium chloride and 9.84 g (15.62 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 150 ml of dimethyl sulfoxide while being heated slightly. At 10° C., 4.03 g (19.52 mmol) of dicyclohexylcarbodiimide is added, and it is stirred for 16 hours at room temperature. The solution is poured into 2000 ml of diethyl ether and stirred for 10 more minutes. The precipitated solid is filtered off, and then the residue is chromatographed on silica gel (mobile solvent: dichloromethane/methanol/aqueous ammonia 10:5:1).

Yield: 16.4 g (79% of theory) of a colorless solid
Water content (Karl-Fischer): 5.4%
Elementary Analysis (relative to the anhydrous substance):

| | | | | | |
|---|---|---|---|---|---|
| Cld.: | C 37.41 | H 3.62 | N 7.83 | F 25.80 | Gd 12.56 |
| Fnd.: | C 37.69 | H 3.56 | N 7.91 | F 25.64 | Gd 12.37 | b) 1H,1H,2H,2H,4H,4H,5H,5H-3-N-[1,4,7-tris-(carboxylatomethyl)-1,4,7,10-tetraazacyclododecane-10-N-(pentanoyl-3-aza-4-oxo-5-methyl-5-yl)]-perfluorotridecylamine, Gd Complex, Methanesulfonic Acid Salt 1.16 g (12.08 mmol) of methanesulfonic acid as well as 2.0 g of palladium catalyst (10% Pd/C) are added to a solution of 16 g (12.08 mmol) of the title compound of Example 2a in 300 ml of ethanol, and it is hydrogenated for 24 hours at room temperature. Catalyst is filtered out, and the filtrate is evaporated to the dry state in a vacuum.

Yield: 15.8 g (quantitative) of a colorless solid
Water content (Karl-Fischer): 7.0%
Elementary Analysis (relative to the anhydrous substance):

| | | | | | |
|---|---|---|---|---|---|
| Cld.: | C 31.66 | H 3.57 | N 8.08 | F 26.60 | Gd 12.95 |
| Fnd.: | C 31.88 | H 3.59 | N 8.14 | F 26.42 | Gd 12.69 | c) 1H,1H,2H,2H,4H,4H,5H,5H-3-N-[1,4,7-tris-(carboxylatomethyl)-1,4,7,10-tetraazacyclododecane-10-N-(pentanoyl-3-aza-4-oxo-5-methyl-5-yl)]-perfluorotridecyl-N-2-(1-O-α-d-mannopyranosyl)-acetamide, Gd Complex 1.72 g (8.33 mmol) of dicyclohexylcarbodiimide as well as 674 mg (6.66 mmol) of triethylamine are added at 0° C. to a solution of 8.9 g (6.66 mmol) of the title compound of Example 2b and 3.99 g (6.66 mmol) of 1-O-α-d-carbonylmethyl-(2,3,4,6-tetra-O-benzyl)mannopyranose (produced according to WO 99/01160 A1) and 767 mg (6.66 mmol) of N-hydroxysuccinimide in 100 ml of dimethylformamide, it is stirred for 3 hours at 0° C. and then for 16 hours at room temperature. Precipitated urea is filtered out, and the filtrate is evaporated to the dry state in a vacuum. The residue is dissolved in 100 ml of methanol, mixed with 2.0 g of palladium catalyst (10% Pd/C) and hydrogenated for 24 hours at room temperature. Catalyst is filtered out, and the filtrate is evaporated to the dry state in a vacuum. The residue is taken up in a little water, insoluble components are filtered out, and the filtrate is then purified by chromatography (RP-18; mobile solvent: gradient that consists of water/acetonitrile).

Yield: 6.1 g (64% of theory) of a colorless solid
Water content (Karl-Fischer): 6.2%
Elementary Analysis (relative to the anhydrous substance):

| | | | | | |
|---|---|---|---|---|---|
| Cld.: | C 35.01 | H 3.84 | N 7.33 | F 24.14 | Gd 11.75 |
| Fnd.: | C 35.23 | H 3.88 | N 7.27 | F 24.01 | Gd 11.59 |

Example 3 a) [1,3-Bis-(2-benzyloxy-1-benzyloxymethyl-ethoxy)-prop-2-yl]-acetic Acid 14.62 g (75 mmol) of bromoacetic acid-tert-butyl ester is added [to] 30.02 g (50 mmol) of 1,3-bis-(2-benzyloxy-1-benzyloxymethyl-ethoxy)-propan-2-ol (Cassel et al., Eur. J. Org. Chem., 2001, 5, 875-896) and 5.6 g (100 mmol) of fine-powder potassium hydroxide as well as a catalytic amount (1 g) of tetra-n-butylammonium hydrogen sulfate in 250 ml of toluene at 0° C., and it is stirred for 2 hours at this temperature as well as for 12 hours at room temperature. The reaction solution is mixed with 500 ml of ethyl acetate and 300 ml of water. The organic phase is separated and washed twice with 300 ml each of water, then dried on magnesium sulfate and evaporated to the dry state in a vacuum. The residue is suspended in a mixture consisting of 400 ml of methanol and 0.5 M sodium hydroxide solution at a 2:1 ratio and then heated for 12 hours to 60° C. The reaction mixture is neutralized for working-up by mixing with Amberlite IR 120 (H⁺ form)-cation exchange resin, exchanger is filtered out, evaporated to the dry state, and chromatographed on silica gel (mobile solvent: ethyl acetate/hexane 1:3).

Yield: 23.5 g (71% of theory) of a colorless wax
Elementary Analysis:

| | | |
|---|---|---|
| Cld.: | C 71.10 | H 7.04 |
| Fnd.: | C 71.29 | H 7.21 | b) N-[2-(Benzyloxycarbonyl)-aminoethyl-N-(1H,1H,2H,2H-perfluorodecyl)-2-[1,3-bis-(2-benzyloxy-1-benzyloxymethyl-ethoxy)-prop-2-oxy]-acetamide 8.05 g (39.04 mmol) of dicyclohexylcarbodiimide is added at 0° C. to a solution of 20 g (31.23 mmol) of the title compound of Example 1a and 20.57 g (31.23 mmol) of the title compound of Example 3a and 3.59 g (31.23 mmol) of N-hydroxysuccinimide in 200 ml of dimethylformamide, and it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20: 1).

Yield: 28.7 g (72% of theory) of a colorless, viscous oil.
Elementary Analysis:

| | | | | |
|---|---|---|---|---|
| Cld.: | C 55.32 | H 4.80 | N 2.19 | F 25.21 |
| Fnd.: | C 55.56 | H 4.87 | N 2.13 | F 26.07 | c) N-(2-Aminoethyl)-N-(1H,1H,2H,2H-perfluorodecyl)-2-[1,3-bis-(2-hydroxy-1-hydroxymethyl-ethoxy)-prop-2-oxy]-acetamide, Methanesulfonic Acid Salt 1.96 g (20.29 mmol) of methanesulfonic acid as well as 4.0 g of palladium catalyst (10% Pd/C) are added to a solution of 26 g (20.29 mmol) of the title compound of Example 3b in 500 ml of ethanol, and it is hydrogenated for 24 hours at room temperature. Catalyst is filtered out, and the filtrate is evaporated to the dry state in a vacuum.

Yield: 17.9 g (quantitative) of a colorless solid
Elementary Analysis:

| | | | | |
|---|---|---|---|---|
| Cld.: | C 32.66 | H 4.00 | N 3.17 | F 36.59 |
| Fnd.: | C 32.89 | H 4.10 | N 3.11 | F 36.41 | d) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-[1,3-bis-(2-hydroxy-1-hydroxymethyl-ethoxy)-prop-2-oxy]-acetamide, Gd Complex 16.8 g (19.07 mmol) of the title compound of Example 3c, 2.19 g (19.07 mmol) of N-hydroxysuccinimide, 1.62 g (38.14 mmol) of lithium chloride and 14.31 g (19.07 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 4.92 g (23.84 mmol) of dicyclohexylcarbodiimide as well as 1.93 g (19.07 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 20.6 g (72% of theory) of a colorless solid
Water content (Karl-Fischer): 6.7%
Elementary Analysis (relative to the anhydrous substance):

| Cld.: | C 36.06 | H 4.25 | N 7.01 | F 23.10 | Gd 11.25 |
|---|---|---|---|---|---|
| Fnd.: | C 36.34 | H 4.32 | N 6.97 | F 22.88 | Gd 11.17 |

Example 4 a) 1,4,7-{Tris(carboxylatomethyl)-10-[(3-aza-4-oxo-hexan-5-ylic)acid-N-1H,1H,2H,2H,4H,4H,5H,5H-3-N-[1,4,7-tris-(carboxylatomethyl)-1,4,7,10-tetraaza-cyclododecane-10-N-(pentanoyl-3-aza-4-oxo-5-methyl-5-yl)]-perfluorotridecylamide}-1,4,7,10-tetraazacyclododecane, Gd Complex 8.1 g (6.31 mmol) of the title compound of Example 2b, 726 mg (6.31 mmol) of N-hydroxysuccinimide, 535 mg (12.62 mmol) of lithium chloride and 3.97 g (6.31 mmol) of 1,4,7-tris-(carboxylatomethyl)-10-[1-carboxy-3-aza-4-oxo-5-methylpentan-5-yl]-1,4,7,10-tetraazacyclododecane, Gd Complex (WO 98/24775, Schering A G, (Example 1)) are dissolved in 100 ml of dimethyl sulfoxide while being heated slightly. At 10° C., 1.63 g (7.89 mmol) of dicyclohexylcarbodiimide as well as 693 mg (6.31 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 6.5 g (56% of theory) of a colorless solid
Water content (Karl-Fischer): 5.8%
Elementary Analysis (relative to the anhydrous substance):

| Cld.: | C 34.72 | H 3.90 | N 9.72 | F 18.67 | Gd 18.18 |
|---|---|---|---|---|---|
| Fnd.: | C 34.94 | H 3.94 | N 9.67 | F 18.59 | Gd 18.01 |

Example 5 a) N-[2-(Benzyloxycarbonyl)-aminoethyl-N-(1H,1H,2H,2H-perfluorodecyl)-2-[2-(2-methoxyethoxy)-ethoxy]-acetamide 8.05 g (39.04 mmol) of dicyclohexylcarbodiimide is added at 0° C. to a solution of 20 g (31.23 mmol) of the title compound of Example 1a and 5.57 g (31.23 mmol) of [2-(2-methoxyethoxy)-ethoxy]-acetic acid (Aldrich) and 3.59 g (31.23 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 19.8 g (79% of theory) of a colorless, viscous oil.
Elementary Analysis:

| Cld.: | C 40.51 | H 3.65 | N 3.50 | F 40.35 |
|---|---|---|---|---|
| Fnd.: | C 40.62 | H 3.68 | N 3.53 | F 40.09 | b) N-(2-Aminoethyl)-N-(1H,1H,2H,2H-perfluorodecyl)-2-[2-(2-methoxyethoxy)-ethoxy]-acetamide, Methanesulfonic Acid Salt 2.28 g (23.73 mmol) of methanesulfonic acid as well as 4.0 g of palladium catalyst (10% Pd/C) are added to a solution of 19 g (23.73 mmol) of the title compound of Example 5a in 500 ml of ethanol, and it is hydrogenated for 24 hours at room temperature. Catalyst is filtered out, and the filtrate is evaporated to the dry state in a vacuum.

Yield: 18.1 g (quantitative) of a colorless solid.
Elementary Analysis:

| Cld.: | C 31.51 | H 3.57 | N 3.67 | F 42.36 |
|---|---|---|---|---|
| Fnd.: | C 31.77 | H 3.59 | N 3.54 | F 42.05 | c) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-[2-(2-methoxyethoxy)-ethoxy]-acetamide, Gd Complex 17.2 g (22.51 mmol) of the title compound of Example 5b, 2.59 g (22.51 mmol) of N-hydroxysuccinimide, 1.91 g (45.02 mmol) of lithium chloride and 14.18 g (22.51 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 5.81 g (28.14 mmol) of dicyclohexylcarbodiimide as well as 2.28 g (22.51 mmol) of triethylamine are added, and it is stirred for 16 hours at room temperature. The solution is poured into 2000 ml of acetone and stirred for 10 more minutes. The precipitated solid is filtered off and then purified by chromatography (RP18; mobile solvent: gradient that consists of water/acetonitrile).

Yield: 21.5 g (70% of theory) of a colorless solid
Water content (Karl-Fischer): 6.4%
Elementary Analysis (relative to the anhydrous substance):

| Cld.: | C 35.71 | H 4.02 | N 7.67 | F 25.72 | Gd 12.30 |
|---|---|---|---|---|---|
| Fnd.: | C 35.79 | H 4.07 | N 7.59 | F 25.63 | Gd 12.27 |

Example 6 a) 1-N-(Benzyloxycarbonyl)-1H,1H,2H,2H,5H,5H,7H,7H,8H,8H-3-aza-4-oxa-6-oxo-perfluorohexadecylamine 17.8 g (140 mmol) of oxalyl chloride is added to 52.22 g (100 mmol) of 2H,2H,4H,4H,5H,5H-3-oxa-perfluorotridecanoic acid (produced according to EP 01/08498) in 500 ml of dichloromethane, and it is stirred for 14 hours at room temperature. It is evaporated to the dry state in a vacuum, the residue is dissolved in 400 ml of dichloromethane, mixed at 0° C. with 23.31 g (120 mmol) of N-benzyloxycarbonyl-ethylenediamine (Atwell et al., *Synthesis*, 1984, 1032-1033) and 10.2 g (100 mmol) of triethylamine, and it is stirred for 24 more hours at room temperature. The reaction solution is mixed with 400 ml of 1N hydrochloric acid and thoroughly stirred for 15 minutes. The organic phase is separated, dried on magnesium sulfate and evaporated to the dry state in a vacuum. The residue is chromatographed on silica gel (mobile solvent: ethyl acetate/hexane 1:2).

Yield: 49.7 g (71% of theory) of a colorless wax
Elementary Analysis:

| | | | | |
|---|---|---|---|---|
| Cld.: | C 37.84 | H 2.74 | N 4.01 | F 46.25 |
| Fnd.: | C 38.02 | H 2.76 | N 3.97 | F 46.12 | b) 1-N-(Benzyloxycarbonyl)-1H,1H,2H,2H,4H,4H,5H,5H,7H,7H,8H,8H-3-aza-6-oxo-perfluorohexadecylamine 48.5 g (69.45 mmol) of the title compound of Example 6a in 150 ml of THF is mixed with 50 ml of 10 M boranedimethyl sulfide (in THF) and refluxed for 5 hours. It is cooled to 0° C., 100 ml of methanol is added in drops, it is stirred for 1 hour at room temperature and then evaporated to the dry state in a vacuum. The residue is taken up in a mixture that consists of 300 ml of ethanol/50 ml of 1 M hydrochloric acid, and it is stirred for 14 hours at 40° C. It is evaporated to the dry state in a vacuum, the residue is taken up in 300 ml of 5% sodium hydroxide solution and extracted three times with 300 ml each of dichloromethane. The combined organic phases are dried on magnesium sulfate, evaporated to the dry state in a vacuum, and the residue is chromatographed on silica gel (mobile solvent: dichloromethane/methanol 10:1).

Yield: 39.8 g (84% of theory) of a colorless solid
Elementary Analysis:

| | | | | |
|---|---|---|---|---|
| Cld.: | C 38.61 | H 3.09 | N 4.09 | F 47.19 |
| Fnd.: | C 38.88 | H 3.14 | N 4.06 | F 46.87 | c) N-[2-(Benzyloxycarbonyl)-aminoethyl-N-(1H,1H,2H,2H,4H,4H,5H,5H-3-oxa-perfluorotridecyl)-2-[2-(2-methoxyethoxy)-ethoxy]-acetamide 7.54 g (36.53 mmol) of dicyclohexylcarbodiimide is added at 0° C. to a solution of 20 g (29.22 mmol) of the title compound of Example 6b and 5.21 g (29.22 mmol) of [2-(2-methoxyethoxy)-ethoxy]-acetic acid (Aldrich) and 3.36 g (29.22 mmol) of N-hydroxysuccinimide in 200 ml of dimethylformamide, and it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 18.3 g (74% of theory) of a colorless, viscous oil.
Elementary Analysis:

| | | | | |
|---|---|---|---|---|
| Cld.: | C 41.24 | H 3.94 | N 3.32 | F 38.24 |
| Fnd.: | C 41.42 | H 3.98 | N 3.33 | F 38.21 | d) N-(2-Aminoethyl)-N-(1H,1H,2H,2H,4H,4H,5H,5H-3-oxa-perfluorotridecyl)-2-[2-(2-methoxy-ethoxy)-ethoxy]-acetamide, Methanesulfonic Acid Salt 2.0 g (20.72 mmol) of methanesulfonic acid as well as 3.0 g of palladium catalyst (10% Pd/C) are added to a solution of 17.5 g (20.72 mmol) of the title compound of Example 6c in 300 ml of ethanol, and it is hydrogenated for 24 hours at room temperature. Catalyst is filtered out, and the filtrate is evaporated to the dry state in a vacuum.

Yield: 16.7 g (quantitative) of a colorless solid.
Elementary Analysis:

| | | | | |
|---|---|---|---|---|
| Cld.: | C 32.76 | H 3.87 | N 3.47 | F 40.04 |
| Fnd.: | C 32.99 | H 3.98 | N 3.35 | F 39.84 | e) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H,5H,5H-3-oxa-perfluorotridecyl)-2-[2-(2-methoxyethoxy)-ethoxy]-acetamide, Gd Complex 14.8 g (18.30 mmol) of the title compound of Example 6d, 2.11 g (18.30 mmol) of N-hydroxysuccinimide, 1.55 g (36.60 mmol) of lithium chloride and 11.52 g (18.30 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 4.72 g (22.88 mmol) of dicyclohexylcarbodiimide as well as 1.85 g (18.30 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 16.6 g (64% of theory) of a colorless solid
Water content (Karl-Fischer): 6.9%
Elementary Analysis (relative to the anhydrous substance):

| | | | | | |
|---|---|---|---|---|---|
| Cld.: | C 36.34 | H 4.19 | N 7.42 | F 24.43 | Gd 11.89 |
| Fnd.: | C 36.49 | H 4.27 | N 7.36 | F 24.28 | Gd 11.78 |

Example 7 a) 6-N-Benzyloxycarbonyl-2-N-(2H,2H,4H,4H,5H,5H-3-oxaperfluorotridecanoyl)-L-lysine 25 g (31.31 mmol) of 6-N-benzyloxycarbonyl-2-N-(2H,2H,4H,4H,5H,5H-3-oxaperfluorotridecanoyl)-L-lysine methyl ester (produced according to EP 03/07274) is dissolved in 200 ml of methanol and 50 ml of 2N potassium hydroxide solution and stirred for 18 hours at room temperature. It is acidified with 2N hydrochloric acid, evaporated to the dry state, and the residue is chromatographed on silica gel (mobile solvent: dichloromethane/methanol 10:1).

Yield: 22.4 g (91% of theory) of a colorless solid.
Elementary Analysis:

| | | | | |
|---|---|---|---|---|
| Cld.: | C 39.81 | H 3.21 | N 3.57 | F 41.17 |
| Fnd.: | C 40.07 | H 3.27 | N 3.49 | F 41.05 | b) [1-O-α-d-(2,3,4,6-Tetra-O-benzyl)mannopyranosyl]-acetamide 11.45 g (90 mmol) of oxalyl chloride is added to 40 g (66.81 mmol) of 1-O-α-d-carbonylmethyl-(2,3,4,6-tetra-O-benzyl)mannopyranose (produced according to WO 99/01160 A1) in 300 ml of dichloromethane, and it is stirred for 14 hours at room temperature. It is evaporated to the dry state in a vacuum, the residue is dissolved in 400 ml of dichloromethane, ammonia gas is introduced into the solution at 0° C. for about 2 hours, and it is stirred for 4 more hours at room temperature. The reaction solution is mixed with 400 ml of 1N hydrochloric acid, and it is thoroughly stirred for 15 minutes. The organic phase is separated, dried on magnesium sulfate and evaporated to the dry state in a vacuum. The residue is chromatographed on silica gel (mobile solvent: ethyl acetate/hexane 1:2).

Yield: 34.1 g (85% of theory) of a colorless oil
Elementary Analysis:

|       | C       | H      | N      |
|-------|---------|--------|--------|
| Cld.: | C 72.34 | H 6.58 | N 2.34 |
| Fnd.: | C 72.69 | H 6.54 | N 2.39 | c) 2-[1-O-α-d-(2,3,4,6-Tetra-O-benzyl)mannopyranosyl]-ethylamine 33 g (55.21 mmol) of the title compound of Example 7b in 100 ml of THF is mixed with 30 ml of 10 M boranedimethyl sulfide (in THF) and refluxed for 5 hours. It is cooled to 0° C., 100 ml of methanol is added in drops, it is stirred for 1 hour at room temperature and then evaporated to the dry state in a vacuum. The residue is taken up in a mixture that consists of 200 ml of ethanol/100 ml of ethanolamine, and it is stirred for 14 hours at 60° C. It is evaporated to the dry state in a vacuum, the residue is taken up in 300 ml of 5% sodium hydroxide solution, and it is extracted three times with 300 ml each of dichloromethane. The combined organic phases are dried on magnesium sulfate, evaporated to the dry state in a vacuum, and the residue is chromatographed on silica gel (mobile solvent: dichloromethane/methanol 10: 1).

Yield: 26.2 g (81% of theory) of a colorless solid
Elementary Analysis:

|       | C       | H      | N      |
|-------|---------|--------|--------|
| Cld.: | C 74.08 | H 7.08 | N 2.40 |
| Fnd.: | C 74.55 | H 7.19 | N 2.31 | d) 6-N-Benzyloxycarbonyl-2-N-(2H,2H,4H,4H,5H,5H-3-oxaperfluorotridecanoyl)-L-lysine-{2-[1-O-α-d-(2,3,4,6-tetra-O-benzyl)mannopyranosyl]-ethyl}-amide 4.93 g (23.90 mmol) of dicyclohexylcarbodiimide is added at 0° C. to a solution of 15 g (19.12 mmol) of the title compound of Example 7a and 11.16 g (19.12 mmol) of the title compound of Example 7c and 2.20 g (19.12 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 19.2 g (74% of theory) of a colorless, viscous oil.
Elementary Analysis:

|       | C       | H      | N      | F       |
|-------|---------|--------|--------|---------|
| Cld.: | C 55.15 | H 4.78 | N 3.11 | F 23.92 |
| Fnd.: | C 55.32 | H 4.82 | N 3.09 | F 23.74 | e) 2-N-(2H,2H,4H,4H,5H,5H-3-Oxaperfluorotridecanyl)-L-lysine-[2-{1-O-α-d-mannopyranosyl)-ethyl]-amide 2.0 g of palladium catalyst (10% Pd/C) is added to a solution of 18.5 g (13.70 mmol) of the title compound of Example 7d in 200 ml of ethanol, and it is hydrogenated for 24 hours at room temperature. Catalyst is filtered out, and the filtrate is evaporated to the dry state in a vacuum.

Yield: 11.8 g (quantitative) of a colorless solid.
Elementary Analysis:

|       | C       | H      | N      | F       |
|-------|---------|--------|--------|---------|
| Cld.: | C 36.50 | H 4.01 | N 4.91 | F 37.75 |
| Fnd.: | C 36.79 | H 3.98 | N 4.87 | F 37.84 | f) 6-N-[1,4,7-Tris-(carboxylatomethyl)-1,4,7,10-tetraazacyclododecane-10-N-(pentanoyl-3-aza-4-oxo-5-methyl-5-yl)]-2-N-(2H,2H,4H,4H,5H,5H-3-oxaperfluorotridecanoyl)-L-lysine-[2-{1-O-α-d-mannopyranosyl)-ethyl]-amide, Gd Complex 11.0 g (12.86 mmol) of the title compound of Example 7e, 1.48 g (12.86 mmol) of N-hydroxysuccinimide, 1.09 g (25.72 mmol) of lithium chloride and 8.10 g (12.86 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 100 ml of dimethyl sulfoxide while being heated slightly. At 10° C., 3.32 g (16.08 mmol) of dicyclohexylcarbodiimide is added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield 13.0 g (64% of theory) of a colorless solid
Water content (Karl-Fischer): 6.9%
Elementary Analysis (relative to the anhydrous substance):

|       | C       | H      | N      | F       | Gd       |
|-------|---------|--------|--------|---------|----------|
| Cld.: | C 36.84 | H 4.26 | N 7.64 | F 22.01 | Gd 10.72 |
| Fnd.: | C 37.03 | H 4.31 | N 7.59 | F 21.95 | Gd 10.62 |

Example 8 a) 6-N-Benzyloxycarbonyl-2-N-(2H,2H,4H,4H,5H,5H-3-oxaperfluorotridecanoyl)-L-lysine{[N-(2S,3R,4R,5R)-2,3,4,5,6-pentahydroxyhexyl]-N-methyl}-amide 4.93 g (23.90 mmol) of dicyclohexylcarbodiimide is added at 0° C. to a solution of 15 g (19.12 mmol) of the title compound of Example 7a and 5.6 g (28.68 mmol) of N-methylglucamine (Aldrich) and 2.20 g (19.12 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 5:1).

Yield: 9.4 g (51% of theory) of a colorless, viscous oil.
Elementary Analysis:

| | | | | |
|---|---|---|---|---|
| Cld.: | C 41.22 | H 4.19 | N 4.37 | F 33.58 |
| Fnd.: | C 41.47 | H 4.30 | N 4.29 | F 33.35 | b) 2-N-(2H,2H,4H,4H,5H,5H-3-Oxaperfluorotridecanoyl)-L-lysine-{[N-(2S,3R,4R,5R)-2,3,4,5,6-pentahydroxyhexyl]-N-methyl}-amide 1.0 g of palladium catalyst (10% Pd/C) is added to a solution of 9.0 g (9.39 mmol) of the title compound of Example 8a in 100 ml of ethanol, and it is hydrogenated for 24 hours at room temperature. Catalyst is filtered out, and the filtrate is evaporated to the dry state in a vacuum.

Yield: 7.8 g (quantitative) of a colorless solid.
Elementary Analysis:

| | | | | |
|---|---|---|---|---|
| Cld.: | C 36.29 | H 4.14 | N 5.08 | F 39.03 |
| Fnd.: | C 36.44 | H 4.17 | N 4.98 | F 38.86 | c) 6-N-[1,4,7-Tris-(carboxylatomethyl)-1,4,7,10-tetraazacyclododecane-10-N-(pentanoyl-3-aza-4-oxo-5-methyl-5-yl)]-2-N-(2H,2H,4H,4H,5H,5H-3-oxaperfluorotridecanoyl)-L-lysine-{[N-(2S,3R,4R,5R)-2,3,4,5,6-pentahydroxyhexyl]-N-methyl}-amide, Gd Complex 7.0 g (8.46 mmol) of the title compound of Example 8b, 974 mg (8.46 mmol) of N-hydroxysuccinimide, 717 mg (16.92 mmol) of lithium chloride and 5.33 g (8.46 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 100 ml of dimethyl sulfoxide while being heated slightly. At 10° C., 2.18 g (10.57 mmol) of dicyclohexylcarbodiimide is added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 7.4 g (57% of theory) of a colorless solid
Water content (Karl-Fischer): 6.1%
Elementary Analysis (relative to the anhydrous substance):

| | | | | | |
|---|---|---|---|---|---|
| Cld.: | C 36.72 | H 4.34 | N 7.79 | F 22.44 | Gd 10.93 |
| Fnd.: | C 36.87 | H 4.36 | N 7.72 | F 22.48 | Gd 10.94 |

Example 9 a) 6-N-Benzyloxycarbonyl-2-N-(2H,2H,4H,4H,5H,5H-3-oxaperfluorotridecanoyl)-L-lysine-(2-{2-[2-(2-methoxyethoxy)-ethoxy]-ethoxy}-ethyl)-amide 4.93 g (23.90 mmol) of dicyclohexylcarbodiimide is added at 0° C. to a solution of 15 g (19.12 mmol) of the title compound of Example 7a and 3.97 g (19.12 mmol) of (2-{2-[2-(2-methoxyethoxy)-ethoxy]-ethoxy}-ethyl)-amine (Whitessides et al., JACS, 1994, 5057-5062) and 2.20 g (19.12 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 10:1).

Yield: 12.2 g (82% of theory) of a colorless, viscous oil.
Elementary Analysis:

| | | | | |
|---|---|---|---|---|
| Cld.: | C 43.17 | H 4.55 | N 4.32 | F 33.17 |
| Fnd.: | C 43.36 | H 4.61 | N 4.27 | F 33.00 | b) 2-N-(2H,2H,4H,4H,5H,5H-3-Oxaperfluorotridecanoyl)-L-lysine-(2-{2-[2-(2-methoxyethoxy)-ethoxy]-ethoxy}-ethyl)-amide 1.0 g of palladium catalyst (10% Pd/C) is added to a solution of 11.5 g (11.81 mmol) of the title compound of Example 9a in 100 ml of ethanol, and it is hydrogenated for 24 hours at room temperature. Catalyst is filtered out, and the filtrate is evaporated to the dry state in a vacuum.

Yield: 9.95 g (quantitative) of a colorless solid.
Elementary Analysis:

| | | | | |
|---|---|---|---|---|
| Cld.: | C 38.63 | H 4.56 | N 5.00 | F 38.47 |
| Fnd.: | C 38.75 | H 4.61 | N 4.93 | F 38.27 | c) 6-N-[1,4,7-Tris-(carboxylatomethyl)-1,4,7,10-tetraazacyclododecane-10-N-(pentanoyl-3-aza-4-oxo-5-methyl-5-yl)]-2-N-(2H,2H,4H,4H,5H,5H-3-oxaperfluorotridecanoyl)-L-lysine-(2-{2-[2-(2-methoxyethoxy)-ethoxy]-ethoxy}-ethyl)-amide, Gd Complex 9.0 g (10.72 mmol) of the title compound of Example 9b, 1.23 g (10.72 mmol) of N-hydroxysuccinimide, 909 mg (21.44 mmol) of lithium chloride and 6.75 g (10.72 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 100 ml of dimethyl sulfoxide while being heated slightly. At 10° C., 2.76 g (13.4 mmol) of dicyclohexylcarbodiimide is added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 10.1 g (62% of theory) of a colorless solid
Water content (Karl-Fischer): 6.0%
Elementary Analysis (relative to the anhydrous substance):

| | | | | | |
|---|---|---|---|---|---|
| Cld.: | C 36.21 | H 4.17 | N 6.87 | F 22.65 | Gd 11.03 |
| Fnd.: | C 36.41 | H 4.22 | N 6.79 | F 22.58 | Gd 10.92 |

Example 10 a) 2H,2H,4H,4H,-3-Oxa-perfluorododecanoic Acid 64.96 g (333.26 mmol) of bromoacetic acid-tert-butyl ester is added at 0° C. to 100 g (222.17 mmol) of 1H,1H-perfluoro-1-nonanol (Apollo) and 24.9 g (444 mmol) of fine-powder potassium hydroxide as well as a catalytic amount (2 g) of tetra-n-butylammonium hydrogen sulfate in 800 ml of toluene, and it is stirred for 2 hours at this temperature as well as for 12 hours at room temperature. The reaction solution is mixed with 1500 ml of ethyl acetate and 800 ml of water. The organic phase is separated and washed twice with 500 ml each of water, then it is dried on magnesium sulfate and evaporated to the dry state in a vacuum. The residue is suspended in a mixture that consists of 1200 ml of methanol and 0.5 M sodium hydroxide solution in a ratio of 2:1 and then heated for 12 hours to 60° C. The reaction mixture is neutralized by mixing with Amberlite IR 120 (H$^+$ form)-cation exchange resin for working up, exchanger is filtered out, it is evaporated to the dry state, and chromatographed on silica gel (mobile solvent: ethyl acetate/hexane 1:3).

Yield: 87 g (77% of theory) of a colorless wax
Elementary Analysis:

| | | | |
|---|---|---|---|
| Cld.: | C 26.00 | H 0.99 | F 63.56 |
| Fnd.: | C 26.22 | H 1.01 | F 63.42 | b) 1-N-(Benzyloxycarbonyl)-1H,1H,2H,2H,5H,5H,7H,7H-3-aza-4-oxa-6-oxo-perfluoropentyldecylamine 17.8 g (140 mmol) of oxalyl chloride is added to 50.81 g (100 mmol) of the title compound of Example 10a in 500 ml of dichloromethane, and it is stirred for 14 hours at room temperature. It is evaporated to the dry state in a vacuum, the residue is dissolved in 400 ml of dichloromethane, mixed at 0° C. with 23.31 g (120 mmol) of N-benzyloxycarbonyl-ethylenediamine (Atwell et al., *Synthesis*, 1984, 1032-1033) and 10.2 g (100 mmol) of triethylamine, and stirred for 24 more hours at room temperature. The reaction solution is mixed with 400 ml of 1N hydrochloric acid and thoroughly stirred for 15 minutes. The organic phase is separated, dried on magnesium sulfate and evaporated to the dry state in a vacuum. The residue is chromatographed on silica gel (mobile solvent: ethyl acetate/hexane 1:2).

Yield: 46.5 g (68% of theory) of a colorless wax
Elementary Analysis:

| | | | | |
|---|---|---|---|---|
| Cld.: | C 36.86 | H 2.50 | N 4.09 | F 47.19 |
| Fnd.: | C 37.00 | H 2.52 | N 4.11 | F 46.97 | c) 1-N-(Benzyloxycarbonyl)-1H,1H,2H,2H,4H,4H,5H,5H,7H,7H-3-aza-6-oxo-perfluoropentadecylamine 45.5 g (66.40 mmol) of the title compound of Example 10b in 150 ml of THF is mixed with 50 ml of 10 M boranedimethyl sulfide (in THF) and refluxed for 5 hours. It is cooled to 0° C., 100 ml of methanol is added in drops, it is stirred for 1 hour at room temperature and then evaporated to the dry state in a vacuum. The residue is taken up in a mixture that consists of 300 ml of ethanol/50 ml of 1 M hydrochloric acid and stirred for 14 hours at 40° C. It is evaporated to the dry state in a vacuum, the residue is taken up in 300 ml of 5% sodium hydroxide solution and extracted three times with 300 ml each of dichloromethane. The combined organic phases are dried on magnesium sulfate, evaporated to the dry state in a vacuum, and the residue is chromatographed on silica gel (mobile solvent: dichloromethane/methanol 10:1).

Yield: 35.2 g (79% of theory) of a colorless solid
Elementary Analysis:

| | | | | |
|---|---|---|---|---|
| Cld.: | C 37.63 | H 2.86 | N 4.18 | F 48.18 |
| Fnd.: | C 37.87 | H 2.90 | N 4.17 | F 48.00 | d) N-[2-(Benzyloxycarbonyl)-aminoethyl-N-(1H,1H,2H,2H,4H,4H-3-oxa-perfluorododecenyl)-2-{2-[2-(2-methoxyethoxy)-ethoxy]-ethoxy}-acetamide 7.69 g (37.29 mmol) of dicyclohexylcarbodiimide is added at 0° C. to a solution of 20 g (29.83 mmol) of the title compound of Example 10c and 6.63 g (29.83 mmol) of {2-[2-(2-methoxyethoxy)-ethoxy]-ethoxy}-acetic acid (Voegtle et al., *Liebigs Ann. Chem.*, 1980, 858-862) and 3.43 g (29.83 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 20.1 g (77% of theory) of a colorless, viscous oil.
Elementary Analysis:

| | | | | |
|---|---|---|---|---|
| Cld.: | C 41.20 | H 4.03 | N 3.20 | F 36.93 |
| Fnd.: | C 41.44 | H 3.98 | N 3.11 | F 36.84 | e) N-(2-Aminoethyl)-N-(1H,1H,2H,2H,4H,4H-3-oxa-perfluorododecyl)-2-{2-[2(2-methoxyethoxy)-ethoxy]-ethoxy}-acetamide, Methanesulfonic Acid Salt 2.09 g (21.72 mmol) of methanesulfonic acid as well as 3.0 g of palladium catalyst (10% Pd/C) are added to a solution of 19.0 g (21.72 mmol) of the title compound of Example 10d in 300 ml of ethanol, and it is hydrogenated for 24 hours at room temperature. Catalyst is filtered out, and the filtrate is evaporated to the dry state in a vacuum.

Yield: 18.2 g (quantitative) of a colorless solid.
Elementary Analysis:

| Cld.: | C 33.02 | H 3.98 | N 3.35 | F 38.61 |
|---|---|---|---|---|
| Fnd.: | C 33.41 | H 3.96 | N 3.25 | F 38.44 | f) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H,4H,4H,-3-oxa-perfluorododecyl)-2-{2-[2-(2-methoxyethoxy)-ethoxy]-ethoxy}-acetamide, Gd Complex 15.8 g (18.9 mmol) of the title compound of Example 10e, 2.18 g (18.9 mmol) of N-hydroxysuccinimide, 1.60 g (37.80 mmol) of lithium chloride and 11.90 g (18.30 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sufoxide while being heated slightly. At 10° C., 4.87 g (23.63 mmol) of dicyclohexylcarbodiimide as well as 1.91 g (18.9 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 16.7 g (61% of theory) of a colorless solid
Water content (Karl-Fischer): 6.9%
Elementary Analysis (relative to the anhydrous substance):

| Cld.: | C 36.42 | H 4.25 | N 7.25 | F 23.89 | Gd 11.63 |
|---|---|---|---|---|---|
| Fnd.: | C 36.71 | H 4.32 | N 7.19 | F 23.67 | Gd 11.51 |

Example 11 a) 1-N-(Benzyloxycarbonyl)-1H,1H,2H,2H,5H,5H,7H,7H,8H,8H-3-aza-4-oxa-6-oxo-perfluorohexadecylamine 17.8 g (140 mmol) of oxalyl chloride is added to 52.21 g (100 mmol) of 2H,2H,4H,4H,5H,5H-3-oxa-perfluorotridecanoic acid (Example 39g of EP 01/08498) in 500 ml of dichloromethane, and it is stirred for 14 hours at room temperature. It is evaporated to the dry state in a vacuum, the residue is dissolved in 400 ml of dichloromethane, mixed at 0° C. with 23.31 g (120 mmol) of N-benzyloxycarbonyl-ethylenediamine (Atwell et al., *Synthesis,* 1984, 1032-1033) and 10.2 g (100 mmol) of triethylamine, and it is stirred for 24 more hours at room temperature. The reaction solution is mixed with 400 ml of 1N hydrochloric acid and thoroughly stirred for 15 minutes. The organic phase is separated, dried on magnesium sulfate and evaporated to the dry state in a vacuum. The residue is chromatographed on silica gel (mobile solvent: ethyl acetate/hexane 1:2).

Yield: 49.6 g (71% of theory) of a colorless wax
Elementary Analysis:

| Cld.: | C 37.84 | H 2.74 | N 4.01 | F 46.25 |
|---|---|---|---|---|
| Fnd.: | C 37.99 | H 2.81 | N 4.05 | F 45.96 | b) 1-N-(Benzyloxycarbonyl)-1H,1H,2H,2H,4H,4H,5H,5H,7H,7H,8H,8H-3-aza-6-oxo-perfluorohexadecylamine 48.0 g (68.73 mmol) of the title compound of Example 11a in 150 ml of THF is mixed with 50 ml of 10 M boranedimethyl sulfide (in THF) and refluxed for 5 hours. It is cooled to 0° C., 100 ml of methanol is added in drops, it is stirred for 1 hour at room temperature and then evaporated to the dry state in a vacuum. The residue is taken up in a mixture that consists of 300 ml of ethanol/50 ml of 1 M hydrochloric acid, and it is stirred for 14 hours at 40° C. It is evaporated to the dry state in a vacuum, the residue is taken up in 300 ml of 5% sodium hydroxide solution, and it is extracted three times with 300 ml each of dichloromethane. The combined organic phases are dried on magnesium sulfate, evaporated to the dry state in a vacuum, and the residue is chromatographed on silica gel (mobile solvent: dichloromethane/methanol 10:1).

Yield: 30.2 g (64% of theory) of a colorless solid
Elementary Analysis:

| Cld.: | C 36.61 | H 3.09 | N 4.09 | F 47.19 |
|---|---|---|---|---|
| Fnd.: | C 36.77 | H 3.14 | N 4.02 | F 46.99 | c) N-[2-(Benzyloxycarbonyl)-aminoethyl-N-(1H,1H,2H,2H,4H,4H,5H,5H-3-oxa-perfluorotridecyl)-2-{2-[2-(2-methoxyethoxy)-ethoxy)-ethoxy}-acetamide 7.42 g (36.59 mmol) of dicyclohexylcarbodiimide is added at 0° C. to a solution of 20 g (29.22 mmol) of the title compound of Example 11b and 6.49 g (29.22 mmol) of {2-[2-(2-methoxyethoxy)-ethoxy]-ethoxy}-acetic acid (Voegtle et al., *Liebigs Ann. Chem.,* 1980, 858-862) and 3.29 g (29.22 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 20.3 g (78% of theory) of a colorless, viscous oil.
Elementary Analysis:

| Cld.: | C 41.90 | H 4.20 | N 3.15 | F 36.35 |
|---|---|---|---|---|
| Fnd.: | C 42.16 | H 4.28 | N 3.12 | F 36.21 | d) N-(2-Aminoethyl)-N-(1H,1H,2H,2H,4H,4H,5H,5H-3-oxa-perfluorotridecyl)-2-{2-[2-(2-methoxy-ethoxy)-ethoxy]-ethoxy}-acetamide, Methanesulfonic Acid Salt 2.06 g (21.38 mmol) of methanesulfonic acid as well as 3.0 g of palladium catalyst (10% Pd/C) are added to a solution of 19.0 g (21.38 mmol) of the title compound of Example 11c in 300 ml of ethanol, and it is hydrogenated for 24 hours at room temperature. Catalyst is filtered out, and the filtrate is evaporated to the dry state in a vacuum.

Yield: 18.2 g (quantitative) of a colorless solid.
Elementary Analysis:

| Cld.: | C 33.89 | H 4.15 | N 3.29 | F 37.97 |
|---|---|---|---|---|
| Fnd.: | C 34.11 | H 4.21 | N 3.10 | F 37.69 | e) N-{[1,4,7-Tris-(carboxylatomethyl)-1,4,7,10-tetraazacyclododecane-10-N-(pentanoyl-3-aza-4-oxo-5-methyl-5-yl)]-2-amino ethyl}-N-(1H,1H,2H,2H,4H,4H,5H,5H-3-oxa-perfluorotridecyl)-2-{2-[2-(2-methoxyethoxy)-ethoxy]-ethoxy}-acetamide, Gd Complex 15.8 g (18.55 mmol) of the title compound of Example 11d, 2.14 g (18.55 mmol) of N-hydroxysuccinimide, 1.57 g (37.10 mmol) of lithium chloride and 11.68 g (18.55 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 4.78 g (23.19 mmol) of dicyclohexylcarbodiimide as well as 1.88 g (18.55 mmol) of triethylamine are added, and it is stirred for 16 hours at room temperature. The solution is poured into 2000 ml of acetone, and it is stirred for 10 more minutes. The precipitated solid is filtered off and then purified by chromatography (RP-18; mobile solvent: gradient that consists of water/acetonitrile).

Yield: 19.8 g (73% of theory) of a colorless solid
Water content (Karl-Fischer): 6.5%
Elementary Analysis (relative to the anhydrous substance):

| Cld.: | C 36.92 | H 4.35 | N 7.18 | F 23.64 | Gd 11.51 |
|---|---|---|---|---|---|
| Fnd.: | C 37.15 | H 4.30 | N 7.07 | F 23.51 | Gd 11.44 |

Example 12 a) N-[2-(Benzyloxycarbonyl)-aminoethyl-N-(1H,1H,2H,2H-perfluorodecyl)-2-(2-{2-[2-(2-methoxyethoxy)-ethoxy]-ethoxy}-ethoxy)-acetamide 8.05 g (39.04 mmol) of dicyclohexylcarbodiimide is added at 0° C. to a solution of 20 g (31.23 mmol) of the title compound of Example 1a and 8.32 g (31.23 mmol) of (2-{2-[2-(2-methoxyethoxy)-ethoxy]-ethoxy}-ethoxy)-acetic acid (Voegtle et al., Liebigs Ann. Chem., 1980, 858-862) and 3.59 g (31.23 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 22.1 g (80% of theory) of a colorless, viscous oil.
Elementary Analysis:

| Cld.: | C 41.90 | H 4.20 | N 3.15 | F 36.35 |
|---|---|---|---|---|
| Fnd.: | C 42.14 | H 4.26 | N 3.11 | F 36.12 | b) N-(2-Aminoethyl)-N-(1H,1H,2H,2H-perfluorodecyl)-2-(2-{2-[2-(2-methoxyethoxy)-ethoxy]-ethoxy}-ethoxy)-acetamide, Methanesulfonic Acid Salt 2.28 g (23.63 mmol) of methanesulfonic acid as well as 4.0 g of palladium catalyst (10% Pd/C) are added to a solution of 21 g (23.63 mmol) of the title compound of Example 12a in 500 ml of ethanol, and it is hydrogenated for 24 hours at room temperature. Catalyst is filtered out, and the filtrate is evaporated to the dry state in a vacuum.

Yield: 20.1 g (quantitative) of a colorless solid.
Elementary Analysis:

| Cld.: | C 33.89 | H 4.15 | N 3.29 | F 37.97 |
|---|---|---|---|---|
| Fnd.: | C 34.08 | H 4.19 | N 3.17 | F 37.65 | c) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-(2-{2-[2-(2-methoxyethoxy)-ethoxy]-ethoxy}-ethoxy)-acetamide, Gd Complex 16.9 g (19.88 mmol) of the title compound of Example 12b, 2.29 g (19.88 mmol) of N-hydroxysuccinimide, 1.68 g (39.76 mmol) of lithium chloride and 12.52 g (19.88 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 5.13 g (24.85 mmol) of dicyclohexylcarbodiimide as well as 2.01 g (19.88 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 18.1 g (62% of theory) of a colorless solid
Water content (Karl-Fischer): 6.8%
Elementary Analysis (relative to the anhydrous substance):

| Cld.: | C 36.92 | H 4.35 | N 7.18 | F 23.64 | Gd 11.51 |
|---|---|---|---|---|---|
| Fnd.: | C 37.11 | H 4.38 | N 7.09 | F 23.51 | Gd 11.44 |

Example 13 a) N-[2-(Benzyloxycarbonyl)-aminoethyl-N-(1H,1H,2H,2H-perfluorodecyl)-2-methoxyacetamide 8.05 g (39.04 mmol) of dicyclohexylcarbodiimide is added at 0° C. to a solution of 20 g (31.23 mmol) of the title compound of Example 1a and 2.81 g (31.23 mmol) of 2-methoxyacetic acid (Aldrich) and 3.59 g (31.23 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 17.1 g (77% of theory) of a colorless, viscous oil.
Elementary Analysis:

| Cld.: | C 38.78 | H 2.97 | N 3.93 | F 45.34 |
|---|---|---|---|---|
| Fnd.: | C 38.94 | H 3.01 | N 3.88 | F 45.22 | b) N-(2-Aminoethyl)-N-(1H,1H,2H,2H-perfluorodecyl)-2-methoxyacetamide, Methanesulfonic Acid Salt 2.23 g (23.16 mmol) of methanesulfonic acid as well as 4.0 g of palladium catalyst (10% Pd/C) are added to a solution of 16.5 g (23.16 mmol) of the title compound of Example 13a in 500 ml of ethanol, and it is hydrogenated for 24 hours at room temperature. Catalyst is filtered out, and the filtrate is evaporated to the dry state in a vacuum.

Yield: 15.1 g (quantitative) of a colorless solid.
Elementary Analysis:

| Cld.: | C 28.50 | H 2.84 | N 4.15 | F 47.89 |
|---|---|---|---|---|
| Fnd.: | C 28.79 | H 2.96 | N 4.09 | F 47.53 | c) N-{[1,4,7-Tris-(carboxylatomethyl)-1,4,7,10-tetraazacyclododecane-10-N-pentanoyl-3-aza-4-oxo-5-methyl-5-yl)]-2-aminoethyl}-N-(1H,1H,2H,2H-perfluorodecyl)-2-methoxyacetamide, Gd Complex 11.7 g (17.29 mmol) of the title compound of Example 13b, 1.99 g (17.29 mmol) of N-hydroxysuccinimide, 1.46 g (34.58 mmol) of lithium chloride and 10.89 g (17.29 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 4.46 g (21.6 mmol) of dicyclohexylcarbodiimide as well as 1.75 g (17.29 mmol) of triethylamine are added, and it is stirred for 16 hours at room temperature. The solution is poured into 2000 ml of acetone, and it is stirred for 10 more minutes. The precipitated solid is filtered off and then purified by chromatography (RP-18; mobile solvent: gradient that consists of water/acetonitrile).

Yield 12.9 g (59% of theory) of a colorless solid
Water content (Karl-Fischer): 6.0%
Elementary Analysis (relative to the anhydrous substance):

| Cld.: | C 34.32 | H 3.64 | N 8.24 | F 27.14 | Gd 13.21 |
|---|---|---|---|---|---|
| Fnd.: | C 34.59 | H 3.69 | N 8.18 | F 26.98 | Gd 13.14 |

Example 14 a) N-[2-(Benzyloxycarbonyl)-aminoethyl-N-(1H,1H,2H,2H-perfluorodecyl)-2-{-2-[2-(2-methoxyethoxy)-ethoxy]-ethoxy}-acetamide 8.05 g (39.04 mmol) of dicyclohexylcarbodiimide is added at 0° C. to a solution of 20 g (31.23 mmol) of the title compound of Example 1a and 6.94 g (31.23 mmol) of {2-[2-(2-methoxyethoxy)-ethoxy]-ethoxy}-acetic acid (Voegtle et al., *Liebigs Ann. Chem.*, 1980, 858-862) and 3.59 g (31.23 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 22.3 g (85% of theory) of a colorless, viscous oil.
Elementary Analysis:

| Cld.: | C 41.24 | H 3.94 | N 3.32 | F 38.24 |
|---|---|---|---|---|
| Fnd.: | C 41.37 | H 3.99 | N 3.27 | F 38.11 | b) N-(2-Aminoethyl)-N-(1H,1H,2H,2H-perfluorodecyl)-2-{-2-[2-(2-methoxyethoxy)-ethoxy]-ethoxy}-acetamide, Methanesulfonic Acid Salt 2.40 g (24.86 mmol) of methanesulfonic acid as well as 4.0 g of palladium catalyst (10% Pd/C) are added to a solution of 21 g (24.86 mmol) of the title compound of Example 14a in 500 ml of ethanol, and it is hydrogenated for 24 hours at room temperature. Catalyst is filtered out, and the filtrate is evaporated to the dry state in a vacuum.

Yield: 20.1 g (quantitative) of a colorless solid.
Elementary Analysis:

| Cld.: | C 32.76 | H 3.87 | N 3.47 | F 40.04 |
|---|---|---|---|---|
| Fnd.: | C 32.88 | H 3.91 | N 3.33 | F 39.89 | c) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-{-2-[2-(2-methoxyethoxy)-ethoxy]-ethoxy}-acetamide, Gd Complex 11.4 g (14.08 mmol) of the title compound of Example 14b, 1.62 g (14.08 mmol) of N-hydroxysuccinimide, 1.19 g (28.12 mmol) of lithium chloride and 8.87 g (14.08 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G (Example 1)), are dissolved in 200 ml of dimethyl sulfoxide while being heated slightly. At 10° C., 3.63 g (17.6 mmol) of dicyclohexylcarbodiimide as well as 1.43 g (14.08 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 13.9 g (71% of theory) of a colorless solid
Water content (Karl-Fischer): 5.7%
Elementary Analysis (relative to the anhydrous substance):

| | | | | | |
|---|---|---|---|---|---|
| Cld.: | C 36.34 | H 4.19 | N 7.42 | F 24.43 | Gd 11.89 |
| Fnd.: | C 36.57 | H 4.22 | N 7.44 | F 24.29 | Gd 11.77 |

Example 15 a) N-[2-(Benzyloxycarbonyl)-aminoethyl-N-(1H,1H, 2H,2H-perfluorodecyl)-2-(2-methoxyethoxy)-acetamide 8.05 g (39.04 mmol) of dicyclohexylcarbodiimide is added at 0° C. to a solution of 20 g (31.23 mmol) of the title compound of Example 1a and 4.19 g (31.23 mmol) of (2-methoxyethoxy)-acetic acid (Aldrich) and 3.59 g (31.23 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 17.5 g (74% of theory) of a colorless, viscous oil.
Elementary Analysis:

| | | | | |
|---|---|---|---|---|
| Cld.: | C 39.70 | H 3.33 | N 3.70 | F 42.70 |
| Fnd.: | C 40.01 | H 3.42 | N 3.66 | F 42.54 | b) N-(2-Aminoethyl)-N-(1H,1H,2H,2H-perfluorodecyl)-2-(2-methoxyethoxy)-acetamide, Methanesulfonic Acid Salt 2.17 g (22.47 mmol) of methanesulfonic acid as well as 3.0 g of palladium catalyst (10% Pd/C) are added to a solution of 17 g (22.47 mmol) of the title compound of Example 15a in 500 ml of ethanol, and it is hydrogenated for 24 hours at room temperature. Catalyst is filtered out, and the filtrate is evaporated to the dry state in a vacuum.

Yield: 16.2 g (quantitative) of a colorless solid.
Elementary Analysis:

| | | | | |
|---|---|---|---|---|
| Cld.: | C 30.09 | H 3.23 | N 3.90 | F 44.96 |
| Fnd.: | C 30.33 | H 3.25 | N 3.84 | F 44.77 | c) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-(2-methoxyethoxy)-acetamide, Gd Complex 11.5 g (16.07 mmol) of the title compound of Example 15b, 1.85 g (16.07 mmol) of N-hydroxysuccinimide, 1.36 g (32.14 mmol) of lithium chloride and 10.12 g (16.07 mmol) of 1,4, 7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 4.14 g (20.08 mmol) of dicyclohexylcarbodiimide as well as 1.63 g (16.07 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 14.2 g (67% of theory) of a colorless solid
Water content (Karl-Fischer): 6.0%
Elementary Analysis (relative to the anhydrous substance):

| | | | | | |
|---|---|---|---|---|---|
| Cld.: | C 35.04 | H 3.84 | N 7.95 | F 26.17 | Gd 12.74 |
| Fnd.: | C 35.38 | H 3.88 | N 7.91 | F 25.99 | Gd 12.63 |

Example 16 a) 1-N-(Benzyloxycarbonyl)-1H,1H,2H,2H,3H,3H, 4H,4H,6H,6H,-4-aza-perfluorotetradecylamine 25.0 g (120 mmol) of N-benzyloxycarbonyl-propylenediamine (Atwell et al., *Synthesis,* 1984, 1032-1033) and 10.2 g (100 mmol) of triethylamine are added to 54.22 g (100 mmol) of methanesulfonic acid-(1H,1H,2H,2H-perfluorodecyl)-ester (Bartsch et al., *Tetrahedron,* 2000, 3291-3302) in 500 ml of acetonitrile, and it is stirred for 48 hours at 60° C. Insoluble components are filtered out from the reaction solution, it is evaporated to the dry state in a vacuum, and the residue is chromatographed on silica gel (mobile solvent: dichloromethane/methanol 20:1).

Yield: 40.7 g (62% of theory) of a colorless wax
Elementary Analysis:

| | | | | |
|---|---|---|---|---|
| Cld.: | C 38.55 | H 2.93 | N 4.28 | F 49.36 |
| Fnd.: | C 38.73 | H 2.89 | N 4.17 | F 49.11 | b) N-[3-(Benzyloxycarbonyl)-aminopropyl-N-(1H, 1H,2H,2H-perfluorodecyl)-2-{-2-[2-(2-methoxy-ethoxy)-ethoxy]-ethoxy}-acetamide 7.99 g (38.74 mmol) of dicyclohexylcarbodiimide is added at 0° C. to a solution of 20 g (30.99 mmol) of the title compound of Example 16a and 6.89 g (30.99 mmol) of {2-[2-(2-methoxyethoxy)-ethoxy]-ethoxy}-acetic acid (Voegtle et al., *Liebigs Ann. Chem.,* 1980, 858-862) and 3.56 g (30.99 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 21.5 g (81% of theory) of a colorless, viscous oil.
Elementary Analysis:

| | | | | |
|---|---|---|---|---|
| Cld.: | C 41.97 | H 4.11 | N 3.26 | F 37.62 |
| Fnd.: | C 42.24 | H 4.18 | N 3.15 | F 37.44 | c) N-(3-Aminopropyl)-N-(1H,1H,2H,2H-perfluorodecyl)-2-{-2-[2-(2-methoxyethoxy)-ethoxy]-ethoxy}-acetamide, Methanesulfonic Acid Salt 2.25 g (23.29 mmol) of methanesulfonic acid as well as 4.0 g of palladium catalyst (10% Pd/C) are added to a solution of 20 g (23.29 mmol) of the title compound of Example 16b in 500 ml of ethanol, and it is hydrogenated for 24 hours at room temperature. Catalyst is filtered out, and the filtrate is evaporated to the dry state in a vacuum.

Yield: 19.2 g (quantitative) of a colorless solid.
Elementary Analysis:

|  | | | | |
|---|---|---|---|---|
| Cld.: | C 33.67 | H 4.05 | N 3.41 | F 39.36 |
| Fnd.: | C 33.94 | H 4.09 | N 3.27 | F 39.11 | d) N-{[1,4,7-Tris-(carboxylatomethyl)-1,4,7,10-tetraazacyclododecane-10-N-(pentanoyl-3-aza-4-oxo-5-methyl-5-yl)]-3-aminopropyl}-N-(1H,1H,2H,2H-perfluorodecyl)-2-{-2-[2-(2-methoxyethoxy)-ethoxy]-ethoxy}-acetamide, Gd Complex 11.3 g (13.80 mmol) of the title compound of Example 16c, 1.59 g (13.80 mmol) of N-hydroxysuccinimide, 1.17 g (27.60 mmol) of lithium chloride and 8.79 g (13.80 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 3.59 g (17.4 mmol) of dicyclohexylcarbodiimide as well as 1.40 g (13.80 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 12.9 g (66% of theory) of a colorless solid
Water content (Karl-Fischer): 6.0%
Elementary Analysis (relative to the anhydrous substance):

|  | | | | | |
|---|---|---|---|---|---|
| Cld.: | C 36.86 | H 4.30 | N 7.34 | F 24.17 | Gd 11.77 |
| Fnd.: | C 36.99 | H 4.37 | N 7.31 | F 24.01 | Gd 11.69 |

Example 17 a) 1-N-(Benzyloxycarbonyl)-1H,1H,2H,2H,3H,3H,4H,4H,6H,6H,7H,7H-5-aza-perfluoropentadecylamine 26.67 g (120 mmol) of N-benzyloxycarbonyl-butylenediamine (Atwell et al., Synthesis, 1984, 1032-1033) and 10.2 g (100 mmol) of triethylamine are added to 54.22 g (100 mmol) of methanesulfonic acid-(1H,1H,2H,2H-perfluorodecyl)-ester (Bartsch et al., Tetrahedron, 2000, 3291-3302) in 500 ml of acetonitrile, and it is stirred for 48 hours at 60° C. Insoluble components are filtered out from the reaction solution, it is evaporated to the dry state in a vacuum, and the residue is chromatographed on silica gel (mobile solvent: dichloromethane/methanol 20:1).

Yield: 39.6 g (59% of theory) of a colorless wax
Elementary Analysis:

|  | | | | |
|---|---|---|---|---|
| Cld.: | C 39.53 | H 3.17 | N 4.19 | F 48.32 |
| Fnd.: | C 39.74 | H 3.21 | N 4.17 | F 48.17 | b) N-[4-(Benzyloxycarbonyl)-aminobutyl-N-(1H,1H,2H,2H-perfluorodecyl)-2-{-2-[2-(2-methxoyethoxy)-ethoxy]-ethoxy}-acetamide 7.71 g (37.4 mmol) of dicyclohexylcarbodiimide is added at 0° C. to a solution of 20 g (29.92 mmol) of the title compound of Example 17a and 6.65 g (29.92 mmol) of {2-[2-(2-methoxyethoxy)-ethoxy]-ethoxy}-acetic acid (Voegtle et al., Liebigs Ann. Chem., 1980, 858-862) and 3.44 g (29.92 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 26.0 g (79% of theory) of a colorless, viscous oil.
Elementary Analysis:

|  | | | | |
|---|---|---|---|---|
| Cld.: | C 42.67 | H 4.27 | N 3.21 | F 37.01 |
| Fnd.: | C 42.85 | H 4.30 | N 3.16 | F 36.87 | c) N-(4-Aminobutyl)-N-(1H,1H,2H,2H-perfluorodecyl)-2-{-2-[2-(2-methoxyethoxy)-ethoxy]-ethoxy}-acetamide 4.0 g of palladium catalyst (10% Pd/C) is added to a solution of 20 g (22.92 mmol) of the title compound of Example 17b in 500 ml of ethanol, and it is hydrogenated for 24 hours at room temperature. Catalyst is filtered out, and the filtrate is evaporated to the dry state in a vacuum.

Yield: 17.0 g (quantitative) of a colorless solid.
Elementary Analysis:

|  | | | | |
|---|---|---|---|---|
| Cld.: | C 37.41 | H 4.23 | N 3.79 | F 43.73 |
| Fnd.: | C 37.59 | H 4.29 | N 3.74 | F 43.61 | d) N-{[1,4,7-Tris-(carboxylatomethyl)-1,4,7,10-tetraazacyclododecane-10-N-(pentanoyl-3-aza-4-oxo-5-methyl-5-yl)]-4-aminobutyl}-N-(1H,1H,2H,2H-perfluorodecyl)-2-{-2-[2-(2-methoxyethoxy)-ethoxy]-ethoxy}-acetamide, Gd Complex 10 g (13.54 mmol) of the title compound of Example 17c, 1.56 g (13.54 mmol) of N-hydroxysuccinimide, 1.14 g (26.08 mmol) of lithium chloride and 8.69 g (13.54 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 3.53 g (17.07 mmol) of dicyclohexylcarbodiimide is added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 11.7 g (60% of theory) of a colorless solid
Water content (Karl-Fischer): 6.5%
Elementary Analysis (relative to the anhydrous substance):

| | | | | | |
|---|---|---|---|---|---|
| Cld.: | C 37.36 | H 4.40 | N 7.26 | F 23.92 | Gd 11.65 |
| Fnd.: | C 37.51 | H 4.44 | N 7.22 | F 23.84 | Gd 11.59 |

Example 18 a) N-[2-(Benzyloxycarbonyl)-aminoethyl-N-(1H,1H,2H,2H,4H,4H-3-oxa-perfluorododecyl)-2-[2-(2-methoxyethoxy)-ethoxy]-acetamide 7.69 g (37.29 mmol) of dicyclohexylcarbodiimide is added at 0° C. to a solution of 20 g (29.83 mmol) of the title compound of Example 10c and 5.32 g (29.83 mmol) of [2-(2-methoxyethoxy)-ethoxy]-acetic acid (Aldrich) and 3.43 g (29.83 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 17.9 g (72% of theory) of a colorless, viscous oil.
Elementary Analysis:

| | | | | |
|---|---|---|---|---|
| Cld.: | C 40.49 | H 3.76 | N 3.37 | F 38.89 |
| Fnd.: | C 40.62 | H 3.81 | N 3.38 | F 38.77 | b) N-(2-Aminoethyl)-N-(1H,1H,2H,2H,4H,4H-3-oxa-perfluorododecyl)-2-[2-(2-methoxyethoxy)-ethoxy]-acetamide, Methanesulfonic Acid Salt 1.98 g (20.50 mmol) of methanesulfonic acid as well as 3.0 g of palladium catalyst (10% Pd/C) are added to a solution of 17.0 g (20.50 mmol) of the title compound of Example 18c in 300 ml of ethanol, and it is hydrogenated for 24 hours at room temperature. Catalyst is filtered out, and the filtrate is evaporated to the dry state in a vacuum.

Yield: 16.3 g (quantitative) of a colorless solid.
Elementary Analysis:

| | | | | |
|---|---|---|---|---|
| Cld.: | C 31.83 | H 3.69 | N 3.53 | F 40.75 |
| Fnd.: | C 31.57 | H 3.78 | N 3.44 | F 40.51 | c) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl }-N-(1H,1H,2H,2H,4H, 4H-3-oxa-perfluorododecyl)-2-[2-(2-methoxyethoxy)-ethoxy]-acetamide, Gd Complex 14.75 g (18.30 mmol) of the title compound of Example 18d, 2.11 g (18.30 mmol) of N-hydroxysuccinimide, 1.55 g (36.60 mmol) of lithium chloride and 11.52 g (18.30 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 200 ml of dimethyl sulfoxide while being heated slightly. At 10° C., 4.72 g (22.88 mmol) of dicyclohexylcarbodiimide as well as 1.85 g (18.30 mmol) of triethylamine are added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 17.6 g (69% of theory) of a colorless solid
Water content (Karl-Fischer): 6.1%
Elementary Analysis (relative to the anhydrous substance):

| | | | | | |
|---|---|---|---|---|---|
| Cld.: | C 35.81 | H 4.06 | N 7.50 | F 24.69 | Gd 12.02 |
| Fnd.: | C 36.04 | H 4.11 | N 7.49 | F 24.52 | Gd 11.94 |

Example 19 a) 1-N-(tert-Butyloxycarbonyl)-1H,1H,2H,2H,4H, 4H,5H,5H,7H,7H,8H,8H-6-aza-3-oxaperfluorohexaadecylamine 6.13 g (30 mmol) of N-tert-butyloxycarbonyl-3-oxa-pentylenediamine (Koenig et al., *Eur. J Org. Chem.*, 2002, 3004-3014) and 2.55 g (25 mmol) of triethylamine are added to 13.56 g (25 mmol) of methanesulfonic acid-(1H,1H,2H,2H-perfluorodecyl)-ester (Bartsch et al., Tetrahedron, 2000, 3291-3302) in 150 ml of acetonitrile, and it is stirred for 48 hours at 60° C. Insoluble components are filtered out from the reaction solution, it is evaporated to the dry state in a vacuum, and the residue is chromatographed on silica gel (mobile solvent: dichloromethane/methanol 20:1).

Yield: 10.9 g (67% of theory) of a colorless wax
Elementary Analysis:

| | | | | |
|---|---|---|---|---|
| Cld.: | C 35.09 | H 3.56 | N 4.31 | F 49.66 |
| Fnd.: | C 35.28 | H 3.64 | N 4.24 | F 49.53 | b) N-[5-(tert-Butyloxycarbonyl)-amino-3-oxapentyl-N-(1H,1H,2H,2H-perfluorodecyl)-2-{-2-[2-(2-methoxyethoxy)-ethoxy]-ethoxy}-acetamide 3.97 g (19.23 mmol) of dicyclohexylcarbodiimide is added at 0° C. to a solution of 10 g (15.38 mmol) of the title compound of Example 19a and 3.42 g (15.38 mmol) of {2-[2-(2-methoxyethoxy)-ethoxy]-ethoxy}-acetic acid (Voegtle et al., *Liebigs Ann. Chem.*, 1980, 858-862) and 1.77 g (15.38 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 9.9 g (75% of theory) of a colorless, viscous oil.
Elementary Analysis:

| | | | | |
|---|---|---|---|---|
| Cld.: | C 39.35 | H 4.60 | N 3.28 | F 37.79 |
| Fnd.: | C 39.57 | H 4.66 | N 3.16 | F 36.55 | c) N-(5-Amino-3-oxapentyl)-N-(1H,1H,2H,2H-perfluorodecyl)-2-{-2-[2-(2-methoxyethoxy)-ethoxy]-ethoxy}-acetamide 50 ml of trifluoroacetic acid is added at 0° C. to a solution of 9.5 g (11.12 mmol) of the title compound of Example 19b in 100 ml of dichloromethane, and for 3 hours at room temperature. It is evaporated to the dry state in a vacuum, and the residue is chromatographed on silica gel (mobile solvent: dichloromethane/methanol 10:1).

Yield: 7.8 g (93% of theory) of a colorless solid.
Elementary Analysis:

| | | | | |
|---|---|---|---|---|
| Cld.: | C 36.62 | H 4.14 | N 3.71 | F 42.81 |
| Fnd.: | C 36.88 | H 4.21 | N 3.55 | F 43.25 | d) N-{[1,4,7-Tris-(carboxylatomethyl)-1,4,7,10-tetraazacyclododecane-10-N-(pentanoyl-3-aza-4-oxo-5-methyl-5-yl)]-5-amino-3-oxapentyl}-N-(1H,1H,2H,2H-perfluorodecyl)-2-{-2-[2-(2-methoxyethoxy)-ethoxy]-ethoxy}-acetamide, Gd Complex 7 g (9.28 mmol) of the title compound of Example 19c, 1.07 g (9.28 mmol) of N-hydroxysuccinimide, 787 mg (18.56 mmol) of lithium chloride and 5.84 g (9.28 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 100 ml of dimethyl sulfoxide while being heated slightly. At 10° C., 2.39 g (11.6 mmol) of dicyclohexylcarbodiimide is added, and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 8.8 g (65% of theory) of a colorless solid
Water content (Karl-Fischer): 6.5%
Elementary Analysis (relative to the anhydrous substance):

| | | | | | |
|---|---|---|---|---|---|
| Cld.: | C 36.92 | H 4.35 | N 7.18 | F 23.64 | Gd 11.51 |
| Fnd.: | C 37.04 | H 4.39 | N 7.15 | F 23.57 | Gd 11.47 |

Example 20 a) 1-N-(tert-Butyloxycarbonyl)-1H,1H,2H,3H,4H,4H,6H,6H,7H,7H-5-aza-dimethyl-[1,3]-dioxolanyl)]-perfluoropentadecylamine 7.81 g (30 mmol) of N-tert-butyloxycarbonyl-[2,3-(2,2-dimethyl-[1,3]-dioxolanyl)]-butylenediamine [produced from (5-aminoethyl-2,2-dimethyl-[1,3]-dioxolan-4-yl)-methylamine (ACROS) analogously to the production of N-tert-butyloxycarbonyl-3-oxa-pentylenediamine (Koenig et al., Eur. J Org. Chem., 2002, 3004-3014)] and 2.55 g (25 mmol) of triethylamine are added to 13.56 g (25 mmol) of methanesulfonic acid-(1H,1H,2H,2H-perfluorodecyl)-ester (Bartsch et al., Tetrahedron, 2000, 3291-3302) in 150 ml of acetonitrile, and it is stirred for 48 hours at 60° C. Insoluble components are filtered out from the reaction solution, it is evaporated to the dry state in a vacuum, and the residue is chromatographed on silica gel (mobile solvent: dichloromethane/methanol 20:1).

Yield: 12.5 g (71% of theory) of a colorless wax
Elementary Analysis:

| | | | | |
|---|---|---|---|---|
| Cld.: | C 37.40 | H 3.85 | N 3.97 | F 45.72 |
| Fnd.: | C 37.66 | H 3.94 | N 3.88 | F 45.61 | b) N-{4-(tert-Butyloxycarbonyl)-amino-[2,3-(2,2-dimethyl-[1,3]-dioxolanyl)]-butyl}-N-(1H,1H,2H,2H-perfluorodecyl)-2-{-2-[2-(2-methoxyethoxy)-ethoxy]-ethoxy}-acetamide 3.65 g (17.7 mmol) of dicyclohexylcarbodiimide is added at 0° C. to a solution of 10 g (14.16 mmol) of the title compound of Example 20a and 3.15 g (14.16 mmol) of {2-[2-(2-methoxyethoxy)-ethoxy]-ethoxy}-acetic acid (Voegtle et al., Liebigs Ann. Chem., 1980, 858-862) and 1.63 g (14.16 mmol) of N-hydroxysuccinimide in 200 ml of dimethylformamide, it is stirred for 3 hours at 0° C. and then for 16 hours at room temperature. Precipitated urea is filtered out, the filtrate is evaporated to the dry state in a vacuum, and the residue is chromatographed on silica gel (mobile solvent: dichloromethane/methanol 20:1).

Yield: 8.9 g (69% of theory) of a colorless, viscous oil.
Elementary Analysis:

| | | | | |
|---|---|---|---|---|
| Cld.: | C 40.89 | H 4.76 | N 3.08 | F 35.47 |
| Fnd.: | C 40.97 | H 4.85 | N 3.00 | F 35.37 | c) N-(4-Amino-2,3-dihydroxybutyl)-N-(1H,1H,2H,2H-perfluorodecyl)-2-{-2-[2-(2-methoxyethoxy)-ethoxy]-ethoxy}-acetamide 50 ml of trifluoroacetic acid is added at 0° C. to a solution of 8.2 g (9.00 mmol) of the title compound of Example 20b in 100 ml of dichloromethane, and for 3 hours at room temperature. It is evaporated to the dry state in a vacuum, and the residue is chromatographed on silica gel (mobile solvent: dichloromethane/methanol 10:1 to 2:1).

Yield: 6.68 g (96% of theory) of a colorless solid.
Elementary Analysis:

| | | | | |
|---|---|---|---|---|
| Cld.: | C 35.85 | H 4.06 | N 3.64 | F 41.92 |
| Fnd.: | C 36.05 | H 4.11 | N 3.60 | F 41.77 | d) N-{[1,4,7-Tris-(carboxylatomethyl)-1,4,7,10-tetraazacyclododecane-10-N-(pentanoyl-3-aza-4-oxo-5-methyl-5-yl)]-(4-amino-2,3-dihydroxybutyl)-N-(1H,1H,2H,2H-perfluorodecyl)-2-{-2-[2-(2-methoxyethoxy)-ethoxy]-ethoxy}-acetamide, Gd Complex 6 g (7.79 mmol) of the title compound of Example 20c, 897 mg (7.79 mmol) of N-hydroxysuccinimide, 660 mg (15.58 mmol) of lithium chloride and 4.90 g (7.79 mmol) of 1,4,7-tris-(carboxylatomethyl)-10-[1-carboxy-3-aza-4-oxo-5-methylpentan-5-yl]-1,4,7,10-tetraazacyclododecane, Gd complex (WO 98/24775, Schering A G, (Example 1)) are dissolved in 100 ml of dimethyl sulfoxide while being heated slightly. At 10° C., 2.01 g (9.74 mmol) of dicyclohexylcarbodiimide is added and it is stirred for 16 hours at room temperature. The solution is poured into 2000 ml of acetone and stirred for 10 more minutes. The precipitated solid is filtered off and then purified by chromatography (RP-18; mobile solvent: gradient that consists of water/acetonitrile).

Yield: 6.9 g (59% of theory) of a colorless solid
Water content (Karl-Fischer): 7.7%
Elementary Analysis (relative to the anhydrous substance):

| Cld.: | C 36.50 | H 4.30 | N 7.09 | F 23.37 | Gd 11.38 |
| Fnd.: | C 36.71 | H 4.35 | N 7.02 | F 23.41 | Gd 11.29 |

Example 21 a) N-{[1,4,7-Tris-(carboxylatomethyl)-1,4,7,10-tetraazacyclododecane-10-N-(butanoyl-4-(R)-carboxylato-4-yl)]-2-aminoethyl }-N-(1H,1H,2H,2H-perfluorodecyl)-2-{-2-[2-(2-methoxyethoxy)-ethoxy]-ethoxy}-acetamide, Gd complex monosodium salt and N-({1,4,7-tris-(carboxylatomethyl)-1,4,7,10-tetraazacyclododecane-10-N-(ethano-[2-(R)-carboxylatoethyl]-yl)}-2-aminoethyl}-N-(1H,1H,2H,2H-perfluorodecyl)-2-{-2-[2-(2-methoxyethoxy)-ethoxy]-ethoxy}-acetamide, Gd Complex Monosodium Salt 2.84 g (3.52 mmol) of the title compound of Example 14b, 448 mg (4.4 mmol) of triethylamine and 3.51 g (4.4 mmol) of 2-(R)-2-[4,7,10-tris-(carboxylatomethyl)-1,4,7,10-tetraazacyclododecan-1-yl]pentanedicarboxylic acid monopentafluorophenyl ester, Gd complex (WO 2005/0014154, EPIX PHARMACEUTICALS, INC., (Example 9: EP-2104-15-Pfp)) are dissolved in 50 ml of dimethyl sulfoxide, mixed with 356 mg (3.52 mmol) of triethylamine, and stirred for 16 hours at room temperature. The solution is poured into 1000 ml of acetone and stirred for another 10 minutes. The precipitated solid is filtered off and then purified by chromatography (RP-18; mobile solvent: gradient that consists of water/acetonitrile). The fractions that contain the product are concentrated by evaporation, dissolved in water, neutralized with 0.1N sodium hydroxide solution and then freeze-dried.

Yield: 2.03 g (39% of theory) of a colorless solid as a 3:2 regioisomeric mixture.
Water content (Karl-Fischer): 9.2%
Elementary Analysis (relative to the anhydrous substance):

| Cld.: | C 35.72 | H 3.97 | N 6.25 | F 24.01 | Gd 11.69 |
| Fnd.: | C 36.01 | H 4.06 | N 6.29 | F 23.89 | Gd 11.46 |

Example 22 a) N-{[1,4,7-Tris-(carboxylatomethyl)-1,4,7,10-tetraazacyclododecane-10-N-(butanoyl-4-(R)-carboxylato-4-yl)]-2-aminoethyl}-N-(1H,1H,2H,2H-perfluorodecyl)-2-(1-O-α-d-mannopyranosyl)-acetamide, Gd Complex Monosodium Salt and N-({1,4,7-Tris-(carboxylatomethyl)-1,4,7,10-tetraazacyclododecane-10-N-(ethano-[2-(R)-carboxylatoethyl]-yl)}-2-aminoethyl)-N-(1H, 1H,2H,2H-perfluorodecyl)-2-(1-O-α-d-mannopyranosyl)-acetamide, Gd Complex Monosodium Salt 2.83 g (3.44 mmol) of the title compound of Example 1c, 436 mg (4.3 mmol) of triethylamine and 3.43 g (4.3 mmol) of 2-(R)-2-[4,7,10-tris-(carboxylatomethyl)-1,4,7,10-tetraazacyclododecan-1-yl]pentane dicarboxylic acid monopentafluorophenyl ester, Gd complex (WO 2005/0014154, EPIX PHARMACEUTICALS, INC., (Example 9: EP-2104-15 Pfp)) are dissolved in 50 ml of dimethyl sulfoxide, mixed with 348 mg (3.44 mmol) of triethylamine, and stirred for 16 hours at room temperature. The solution is poured into 1000 ml of acetone and stirred for 10 more minutes. The precipitated solid is filtered off and then purified by chromatography (RP-18; mobile solvent: gradient that consists of water/acetonitrile). The fractions containing the product are concentrated by evaporation, dissolved in water, neutralized with 0.1N sodium hydroxide solution and then freeze-dried.

Yield: 1.64 g (32% of theory) of a colorless solid as a 3:2 regioisomeric mixture.
Water content (Karl-Fischer): 8.8%
Elementary Analysis (relative to the anhydrous substance):

| Cld.: | C 34.42 | H 3.63 | N 6.17 | F 23.73 | Gd 11.55 |
| Fnd.: | C 34.66 | H 3.60 | N 6.09 | F 23.78 | Gd 11.39 |

Example 23 a) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-{-2-[2-(2-methoxyethoxy)-ethoxy]-ethoxy}-acetamide, Trisodium Salt 10 g (7.13 mmol) of the title compound of Example 14c is dissolved in a mixture that consists of 100 ml of water and 30 ml of isopropanol, mixed with 2.25 g (24.96 mmol) of oxalic acid and heated for 5 hours to 100° C. After cooling to room temperature, precipitated solid is and then purified by chromatography (RP-18; mobile solvent: gradient that consists of water/acetonitrile). The fractions that contain the product are concentrated by evaporation, dissolved in water, set at a pH of 10 with 0.1N sodium hydroxide solution and then freeze-dried.

Yield: 7.39 g (77% of theory) of a colorless solid
Water content (Karl-Fischer): 8.2%
Elementary Analysis (relative to the anhydrous substance):

| | | | | |
|---|---|---|---|---|
| Cld.: | C 38.94 | H 4.49 | N 7.95 | F 26.18 |
| Fnd.: | C 39.03 | H 4.44 | N 7.98 | F 25.89 | b) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H, 1H,2H,2H-perfluorodecyl)-2-{-2-[2-(2-methoxyethoxy)-ethoxy]-ethoxy}-acetamide, Dy Complex 2.0 g (1.49 mmol) of the title compound of Example 23a is dissolved in 50 ml of water and 1 ml of acetic acid, mixed with 441 mg (1.64 mmol) of dysprosium chloride and stirred for 6 hours at 80° C. It is neutralized with ammonia, evaporated to the dry state and then purified by chromatography (RP-18; mobile solvent: gradient that consists of water/acetonitrile).

Yield: 1.78 g (84% of theory) of a colorless solid
Water content (Karl-Fischer): 6.2%
Elementary Analysis (relative to the anhydrous substance):

| | | | | | |
|---|---|---|---|---|---|
| Cld.: | C 36.19 | H 4.18 | N 7.39 | F 24.33 | Dy 12.24 |
| Fnd.: | C 36.32 | H 4.24 | N 7.30 | F 24.19 | Dy 12.16 |

Example 24 a) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-{-2-[2-(2-methoxyethoxy)-ethoxy]-ethoxy}-acetamide, Yb Complex 2.0 g (1.49 mmol) of the title compound of Example 23a is dissolved in 50 ml of water and 1 ml of acetic acid, mixed with 458 mg (1.64 mmol) of ytterbium chloride and stirred for 6 hours at 80° C. It is neutralized with ammonia, evaporated to the dry state and then purified by chromatography (RP-18; mobile solvent: gradient that consists of water/acetonitrile).

Yield: 1.84 g (86% of theory) of a colorless solid
Water content (Karl-Fischer): 6.9%
Elementary Analysis (relative to the anhydrous substance):

| | | | | | |
|---|---|---|---|---|---|
| Cld.: | C 35.91 | H 4.14 | N 7.33 | F 24.14 | Yb 12.93 |
| Fnd.: | C 36.05 | H 4.19 | N 7.31 | F 24.00 | Yb 12.79 |

Example 25 a) N-{[1,4,7-Tris-(carboxylatomethyl)-1,4,7,10-tetraazacyclododecane-10-N-(pentanoyl-3-aza-4-oxo-5-methyl-5-yl)]-2-aminoethyl}-N-(1H,1H,2H,2H-perfluorodecyl)-2-{-2-[2-(2-methoxyethoxy)-ethoxy]-ethoxy}-acetamide, Y-Complex 2.0 g (1.49 mmol) of the title compound of Example 23a is dissolved in 50 ml of water and 1 ml of acetic acid, mixed with 320 mg (1.64 mmol) of yttrium chloride and stirred for 6 hours at 80° C. It is neutralized with ammonia, evaporated to the dry state and then purified by chromatography (RP-18; mobile solvent: gradient that consists of water/acetonitrile).

Yield: 1.56 g (79% of theory) of a colorless solid
Water content (Karl-Fischer): 5.5%
Elementary Analysis (relative to the anhydrous substance):

| | | | | | |
|---|---|---|---|---|---|
| Cld.: | C 38.32 | H 4.42 | N 7.82 | F 25.76 | Y 7.09 |
| Fnd.: | C 38.56 | H 4.51 | N 7.88 | F 25.65 | Y 6.98 |

Example 26 a) 10-(5-Oxo-tetrahydrofuran-2-ylmethyl)-1,4,7-tris (carboxymethyl)-1,4,7,10-tetraazacyclododecane 8.3 g (207.6 mmol) of sodium hydroxide is added to 12.0 g (34.6 mmol) of 1,4,7-tris(carboxymethyl)-1,4,7,10-tetraazacyclododecane (D03A) in 50 ml of water. A solution that consists of 5.02 g (43.25 mmol) of 3-oxiranylpropionic acid (Dakoji et al., *J. Am. Chem. Soc.*, 1996, 10971-10979) in 50 ml of n-butanol/50 ml of 2-propanol is added in drops thereto, and the solution is heated for 24 hours to 80° C. The reaction solution is evaporated to the dry state in a vacuum, the residue is mixed with 300 ml of water, and a pH of 3 is set with 3N hydrochloric acid. Then, it is extracted three times with 200 ml each of n-butanol, the combined butanol phases are evaporated to the dry state in a vacuum, and the residue is purified by chromatography (RP-18; mobile solvent: gradient that consists of water/acetonitrile).

Yield: 13.6 g (79% of theory) of a colorless solid
Water content (Karl-Fischer): 10.4%
Elementary Analysis (relative to the anhydrous substance):

| | | | |
|---|---|---|---|
| Cld.: | C 51.34 | H 7.26 | N 12.60 |
| Fnd.: | C 51.63 | H 7.05 | N 12.44 | b) 10-(5-Oxo-tetrahydrofuran-2-ylmethyl)-1,4,7-tris (carboxymethyl)-1,4,7,10-tetraazacyclododecane, Gd Complex 12.0 g (24.2 mmol) of the title compound of Example 26a is dissolved in 100 ml of water and 1 ml of acetic acid, mixed with 4.39 g (12.1 mmol) of gadolinium oxide and stirred for 6 hours at 80° C. The solution is filtered, evaporated to the dry state, and then purified by chromatography (RP-18; mobile solvent: gradient that consists of water/acetonitrile).

Yield: 13.8 g (89% of theory) of a colorless solid
Water content (Karl-Fischer): 6.5%
Elementary Analysis (relative to the anhydrous substance):

| | | | | |
|---|---|---|---|---|
| Cld.: | C 38.12 | H 4.88 | N 9.36 | Gd 26.26 |
| Fnd.: | C 38.26 | H 4.89 | N 9.21 | Gd 26.09 | c) N-{[1,4,7-Tris-(carboxylatomethyl)-1,4,7,10-tetraazacyclododecane-10-N-(pentanoyl-4-hydroxy-5-yl)]-2-aminoethyl}-N-(1H,1H,2H,2H-perfluorodecyl)-2-{-2-[2-(2-methoxyethoxy)-ethoxy]-ethoxy}-acetamide, Gd Complex 2.84 g (3.52 mmol) of the title compound of Example 14b and 3.38 g (5.28 mmol) of the title compound of Example 26b are dissolved in 50 ml of methanol, mixed with 356 mg (3.52 mmol) of triethylamine, and stirred for 48 hours at a temperature of 50° C. It is evaporated to the dry state and then purified by chromatography (RP-18; mobile solvent: gradient that consists of water/acetonitrile).

Yield: 3.27 g (66% of theory) of a colorless solid
Water content (Karl-Fischer): 6.9%
Elementary Analysis (relative to the anhydrous substance):

| | | | | | |
|---|---|---|---|---|---|
| Cld.: | C 36.70 | H 4.31 | N 6.42 | F 24.67 | Gd 12.01 |
| Fnd.: | C 36.77 | H 4.38 | N 6.33 | F 24.59 | Gd 11.96 |

Example 27 a) 1H,1H,2H,2H,4H,4H,5H,5H—3-N-[1,4,7-Tris-(carboxylatomethyl)-1,4,7,10-tetraazacyclododecane-10-N-(pentanoyl-3-aza-4-oxo-5-methyl-5-yl)]-perfluorotridecyl-N-{-2-[2-(2-methoxyethoxy)-ethoxy]-ethoxy}-acetamide, Gd Complex 2.58 g (12.5 mmol) of dicyclohexylcarbodiimide, as well as 1.01 g (10 mmol) of triethylamine are added to a solution of 12.14 g (10 mmol) of the title compound of Example 2b and 2.22 g (10 mmol) of {2-[2-(2-methoxyethoxy)-ethoxy]-ethoxy}-acetic acid (Voegtle et al., *Liebigs Ann. Chem.*, 1980, 858-862) and 1.15 g (10 mmol) of N-hydroxysuccinimide in 100 ml of dimethylformamide at 0° C., it is stirred for 3 hours at 0° C. and then for 16 hours at room temperature. Precipitated urea is filtered out, and the filtrate is evaporated to the dry state in a vacuum. The residue is taken up in a little water, insoluble components are filtered out, and the filtrate is then purified by chromatography (RP-18; mobile solvent: gradient that consists of water/acetonitrile).

Yield 8.2 g (58% of theory) of a colorless solid
Water content (Karl-Fischer): 6.2%
Elementary analysis (relative to the anhydrous substance):

| | | | | | |
|---|---|---|---|---|---|
| Cld.: | C 36.34 | H 4.19 | N 7.42 | F 24.43 | Gd 11.89 |
| Fnd.: | C 36.55 | H 4.27 | N 7.33 | F 24.21 | Gd 11.70 |

Example 28 a) 1H,1H,2H,2H,4H,4H,5H,5H—3-N-[1,4,7-Tris-(carboxylatomethyl)-1,4,7,10-tetraazacyclododecane-10-N-(pentanoyl-3-aza-4-oxo-5-methyl-5-yl)]-perfluorotridecyl-N-{-2-[2-(2-methoxyethoxy)-ethoxy]-ethoxy}-acetamide, Trisodium Salt 10 g (7.11 mmol) of the title compound of Example 27a is dissolved in a mixture that consists of 100 ml of water and 30 ml of isopropanol, mixed with 2.25 g (24.96 mmol) of oxalic acid and heated for 5 hours to 100° C. After cooling to room temperature, precipitated solid is filtered out and then purified by chromatography (RP-18; mobile solvent: gradient that consists of water/acetonitrile). The fractions that contain the product are concentrated by evaporation, dissolved in water, set at a pH of 8 with 0.1 N sodium hydroxide solution and then freeze-dried.

Yield 8.64 g (91% of theory) of a colorless solid
Water content (Karl-Fischer): 7.5%
Elementary analysis (relative to the anhydrous substance):

| | | | | |
|---|---|---|---|---|
| Cld.: | C 38.94 | H 4.49 | N 7.95 | F 26.18 |
| Fnd.: | C 38.88 | H 4.40 | N 7.65 | F 25.77 | b) 1H,1H,2H,2H,4H,4H,5H,5H—3-N-[1,4,7-Tris-(carboxylatomethyl)-1,4,7,10-tetraazacyclododecane-10-N-(pentanoyl-3-aza-4-oxo-5-methyl-5-yl)]-perfluorotridecyl-N-{-2-[2-(2-methoxyethoxy)-ethoxy]-ethoxy}-acetamide, Y Complex 2.0 g (1.50 mmol) of the title compound of Example 28a is dissolved in 50 ml of water and 1 ml of acetic acid, mixed with 320 mg (1.64 mmol) of yttrium chloride and stirred for 6 hours at 80° C. It is neutralized with ammonia, evaporated to the dry state and then purified by chromatography (RP-18; mobile solvent: gradient that consists of water/acetonitrile).

Yield 1.43 g (72% of theory) of a colorless solid
Water content (Karl-Fischer): 5.0%
Elementary analysis (relative to the anhydrous substance):

| | | | | | |
|---|---|---|---|---|---|
| Cld.: | C 38.32 | H 4.42 | N 7.82 | F 25.76 | Y 7.09 |
| Fnd.: | C 38.48 | H 4.55 | N 7.75 | F 25.66 | Y 6.96 |

Example 29

Relaxivity

The T1 and T2 relaxation times of water and plasma (bovine) with increasing concentrations of the gadolinium complexes of the title substances of Examples 1d, 5c, 14c, 15c contained therein were determined at 40° C. with use of an NMR pulse spectrometer (Minispec PC 20) at 0.47 T. The results are set forth in Table 1.

Example 30

Acute Toxicity after One-Time Intravenous Administration in Mice (Preliminary)

After intravenous administration of the gadolinium complexes of the title substances of Examples 1d, 5c, 14c, 15c in mice (n=3; rate of injection: 2 ml/min), the acute systemic compatibility ($LD_{50}$) was determined preliminarily. In each case, several dosages with an observation period of 7 days were examined. The acute toxicities that are to be expected can be seen in Table 1.

Example 31

Excretion After Intravenous Administration in Rats

After intravenous administration of 50 μmol of total gadolinium/kg of body weight of the gadolinium complexes of the title substances of Examples 1d, 5c, 14c, 15c in rats (n=3), the metal content was determined in fractions up to 14 days after administration by means of atom emission spectrometry (ICP-AES) in the excretion media of urine and feces, as well as in the body (the rest of the body). The results are presented in Table 1.

Example 32

Plasma Kinetics After Intravenous Administration in Rats

After intravenous administration of 50 µmol of total gadolinium/kg of body weight of the gadolinium complexes of the title substances of Examples 1d, 5c, 14c, 15c in rats (n=3), blood samples were taken via a catheter in the common carotid artery at different points in time (8 hours to 24 hours p.i.), the metal content was determined by means of atom emission spectrometry (ICP-AES) and converted to plasma values via a conversion factor (0.625). The elimination half-life was calculated by means of special software (WinNonlin) from the plasma concentrations. The results are presented in Table 1.

Example 33

Figure 2:
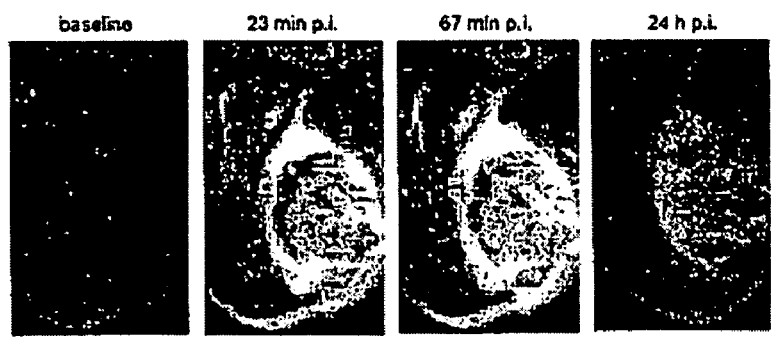

Visualization (MRT) of Lymph Node Metastases and Primary Tumors After Intravenous Administration of the Contrast Medium in VX2-Tumor-Carrying Rabbits The pictures of FIGS. 1 and 2 show MR images of iliac lymph nodes precontrast as well as up to 24 hours after intravenous administration of 50 µmol of Gd/kg of body weight of the title substance of Example 1d) in rabbits with i.m. implanted VX2 tumors. The $T_1$-weighted turbo-spin-echo images illustrate the strong signal rise in healthy lymph node tissue at early points in time after contrast medium administration (15 to 60 minutes p.i.). Zones where there was no signal rise within the lymph node were diagnosed as metastases and confirmed histologically (H/E staining of the lymph node sections) (FIG. 1).

Surprisingly enough, as early as immediately after administration, a clear enhancement in the primary tumor (especially in the periphery) could also be observed (FIG. 2). At later times (24 hours p.i.), this enhancement also propagates toward the center of the tumor.

Example 34

Figure 3:
FIG. 3 shows aorta images using the compound of Example 14c.
Figure 3:
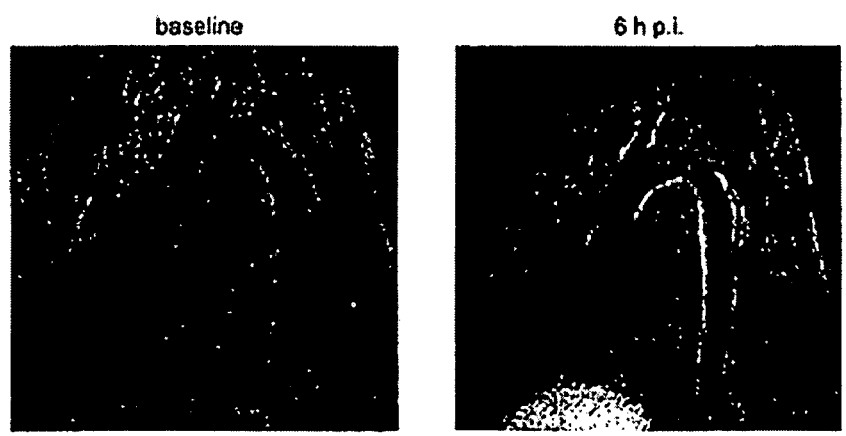

MRT Visualization of Arteriosclerotic Plaque After Intravenous Administration of the Contrast Medium in Rats The pictures of FIG. 3 show MR images of the aorta 6 or 24 hours after intravenous administration of 50 µmol of Gd/kg of body weight of the title substances from Example 1d) and Example 14c in Watanabe rabbits (WHHL rabbits; genetically-induced arteriosclerosis) and in control animals without arteriosclerosis (white New Zealanders). The $T_1$-weighted Inversion-Recovery-Images (IR-TFL, TR/TE/TI=300/4.0/120 ms, α 20°) illustrate a strong signal rise in the arteriosclerotic plaque of WHHL rabbits, but not in the baseline images or in the vascular wall of the healthy control animals. The localization of the plaque, especially in the aortic arch as well as in the vascular passages, was confirmed by means of Sudan-3 staining. With this test, the suitability of the compounds according to the invention as markers for arteriosclerotic plaque could be shown.

Example 35

Figure 4:
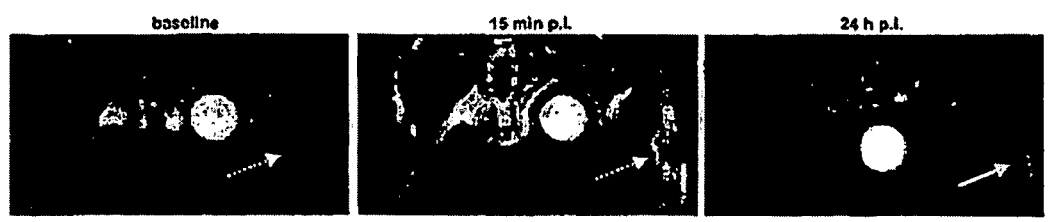
FIG. 4 shows images of inflammatory muscle lesions using the compound of Example 14c.

MRT Visualization of Inflammatory Lesions and Necrotic Areas After Intravenous Administration of the Contrast Medium in Rats By way of example, the pictures of FIG. 4 show MR images of inflammatory muscle lesions as well as necrotic areas at different points in time after intravenous administration of 50 µmol of Gd/kg of body weight of the title substance of Example 14c in rats. The inflammation/necrosis was induced by intravenous administration of Rose Bengal (20 mg/kg; 24 hours before the administration of contrast medium) and subsequent 20-minute irradiation with a xenon lamp. The $T_1$-weighted turbo-spin-echo images (1.5 T; sequence: $T_1$-TSE; TR 451 ms, TE 8.7 ms) illustrate the strong signal rise in the inflammatorily altered tissue early on (up to 60 minutes p.i.) as well as the delayed signal rise in the central necrosis at time 24 hours p.i.

Example 36

MRT Visualization of Lymph Nodes After Intravenous Administration of the Contrast Medium in Rats By way of example, the pictures show MR images of popliteal lymph nodes at different points in time after intravenous administration of 50 µmol of Gd/kg of body weight of the title substance from Example 5c), title substance from Example 14c) and title substance from Example 15c) in rats. The $T_1$-weighted turbo-spin-echo images (1.5T; sequence: T1-TSE; TR 451 ms, TE 8.7 ms) illustrate the strong signal rise in the functional lymph node tissue at early points in time (up to 60 minutes p.i.).

TABLE 1

Physicochemical and Experimental Data Regarding the Example Substances.

| Compound from Example No. | Relaxivity [1/(mmol * s)] | Body Retention 14 days [%] | Elimination Half-Life of Blood | Gd Content of Blood 24 Hours p.i. [%] | $LD_{50}$ Mouse [mmol/kg] |
|---|---|---|---|---|---|
| 1 | R1(w): 22.7<br>R1(p): 25.8<br>R2(w): 15.8<br>R2(p): 29.8 | 0.0% | 4.8 hours | 0.7% | >10 |
| 5 | R1(w): 18.9<br>R1(p): 24.8<br>R2(w): 23.9<br>R2(p): 32.8 | 0.0% | 0.8 hour | 0.0% | |
| 14 | R1(w): 18.6<br>R1(p): 25.5<br>R2(w): 21.6<br>R2(p): 33.5 | 0.0% | 1.1 hours | 0.0% | 7.5 |
| 15 | R1(w): 17.2<br>R1(p): 24.6<br>R2(w): 15.1<br>R2(p): 33.2 | 0.0% | 4.8 hours | 0.2% | >10 |

R1(w) = R1-relaxivity in water;
R1(p) = R1(w) = R1-relaxivity in plasma;
R2(w) = R2-relaxivity in water;
R2(p) = R1(w) = R2-relaxivity in plasma Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102005033902.6, filed Jul. 15, 2005, and U.S. Provisional Application Ser. No. 60/701,032, filed Jul. 21, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A perfluoroalkyl-containing complexes with a nitrogen-containing linker structure of formula I $$K-L-X-R_f \quad | \quad Q-R \qquad (I)$$

in which
Q is a direct bond,
R means a polar radical that is
    a carbon chain with 1-30 C atoms that is bonded via —CO—, —NR$^7$— or a direct bond to linker L,
        which can be straight or branched, saturated or unsaturated, and
    which
        optionally is interrupted by 1-10 oxygen atoms, 1-5 —NHCO groups, 1-5 —CONH groups, 1-2 sulfur atoms, 1-5 —NH groups or 1-2 phenylene groups, which optionally can be substituted by 1-2 —OH groups, 1-2 —NH$_2$ groups, 1-2 —COOH groups, or 1-2 —SO$_3$H groups,
    and which
        optionally is substituted by 1-10 —OH groups, 1-5 —COOH groups, 1-2 SO$_3$H groups, 1-5 —NH$_2$ groups, or 1-5 C$_1$-C$_4$-alkoxy groups,
R$^7$ means H or C$_1$-C$_4$-alkyl,
R$_f$ is a perfluorinated, straight-chain or branched carbon chain with the formula —C$_n$F$_{2n}$E, in which E represents a terminal fluorine, chlorine, bromine, iodine or hydrogen atom, and n stands for the numbers 4-30, K stands for a metal complex of formula II, in which
R$_1$ means a hydrogen atom or a metal ion equivalent of atomic numbers 21-29, 31-33, 37-39, 42-44, 49 or 57-83,
    provided that at least two R$^1$ stand for metal ion equivalents,
R$^2$ and R$^3$, independently of one another, represent hydrogen, C$_1$-C$_7$-alkyl, benzyl, phenyl, —CH$_2$OH or —CH$_2$OCH$_3$, and
U stands for a C$_1$—C$_{12}$-alkylene group that optionally is interrupted by one or more oxygen atoms, 1 to 3 —NHCO groups, or 1 to 3 —CONH groups and/or is substituted by 1 to 3
    —(CH$_2$)$_{0-5}$COOH groups, wherein ω stands for the binding site to —CO—,
and free acid groups, optionally present in radical K, can optionally be present as salts of organic and/or inorganic bases or amino acids or amino acid amides,
and L represents a radical IXc)

$$\alpha\text{-NH}-(CH_2)_{q'}-CH-CO\text{-}\beta \quad | \quad NH \quad | \quad \gamma \qquad (IXc)$$

wherein
q' is 1,2,3 or 4,
wherein α means the binding site of L to complex K, β is the binding site of L to radical Q, and γ represents the binding site of L to radical X,
and
X stands for a group of formula (VI)

$$\rho\text{-y}-(CH_2)_s\text{-}(G)_r\text{-}(CH_2)_{s'}\text{-}\zeta \qquad (X)$$

wherein Y means a direct bond,
wherein R$^6$ stands for —H or a straight or branched, saturated or unsaturated
    C$_1$-C$_{15}$ carbon chain, which can be interrupted by 1-4 O atoms, 1-3 —NHCO groups, 1-3 —CONH groups, 1-2 —SO$_2$ groups, 1-2 sulfur atoms, 1-3 —NH groups or 1-2 phenylene groups,
        which optionally can be substituted by 1-2 OH groups, 1-2 NH$_2$ groups, 1-2 —COOH groups or 1-2 —SO$_3$H groups,
    and which optionally is substituted by 1-10 OH groups, 1-5 —COOH groups, 1-2 —SO$_3$H groups, 1-5 NH$_2$ groups, or 1-5 C$_1$-C$_4$-alkoxy groups,
and G means either —O— or —SO$_2$—,
s and s', independently of one another, mean 1 or 2, t means 0, and ρ represents the binding site of X to L and ξ represents the binding site of X to $R_f$.

2. A metal complex according to claim 1, wherein the metal ion equivalent $R^1$ is an element of atomic numbers 21-29, 39, 42, 44 or 57-83.

3. A metal complex according to claim 1, wherein the metal ion equivalent $R^1$ is an element of atomic numbers 27, 29, 31-33, 37-39, 43, 49, 62, 64, 70, 75 or 77.

4. A metal complex according to claim 1, wherein $R^2$ and $R^3$, independently of one another, mean hydrogen or $C_1$-$C_4$-alkyl.

5. A metal complex according to claim 1, wherein E means a fluorine atom in the formula —$C_nF_{2n}E$.

6. A pharmaceutical composition comprising a metal complex according to claim 1, and a galenically acceptable additive or carrier.

* * * * *

UNITED STATES PATENT AND TRADEMARK OFFICE
CERTIFICATE OF CORRECTION

PATENT NO. : 7,618,957 B2  Page 1 of 1
APPLICATION NO. : 11/487604
DATED : November 17, 2009
INVENTOR(S) : Schirmer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 315 days.

Signed and Sealed this

Twenty-sixth Day of October, 2010

David J. Kappos
*Director of the United States Patent and Trademark Office*